United States Patent
Xia et al.

(10) Patent No.: US 12,334,207 B2
(45) Date of Patent: Jun. 17, 2025

(54) AUTOMATIC APPROACH TO ESTABLISH DENTAL OCCLUSION FOR 1-PIECE, 2-PIECE, AND 3-PIECE MAXILLARY ORTHOGNATHIC SURGERIES

(71) Applicant: THE METHODIST HOSPITAL SYSTEM, Houston, TX (US)

(72) Inventors: James Jiong Xia, Houston, TX (US); Jaime Gateno, Bellaire, TX (US); Peng Yuan, Princeton, NJ (US); Han Deng, Houston, TX (US)

(73) Assignee: THE METHODIST HOSPITAL SYSTEM, Houston, TX (US)

( * ) Notice: Subject to any disclaimer, the term of this patent is extended or adjusted under 35 U.S.C. 154(b) by 488 days.

(21) Appl. No.: 17/765,880

(22) PCT Filed: Oct. 12, 2020

(86) PCT No.: PCT/US2020/055263
§ 371 (c)(1),
(2) Date: Apr. 1, 2022

(87) PCT Pub. No.: WO2021/072378
PCT Pub. Date: Apr. 15, 2021

(65) Prior Publication Data
US 2022/0351829 A1    Nov. 3, 2022

Related U.S. Application Data

(60) Provisional application No. 62/913,393, filed on Oct. 10, 2019.

(51) Int. Cl.
*G16H 20/40*    (2018.01)
*A61C 13/34*    (2006.01)
*A61C 19/05*    (2006.01)

(52) U.S. Cl.
CPC ............. *G16H 20/40* (2018.01); *A61C 13/34* (2013.01); *A61C 19/05* (2013.01)

(58) Field of Classification Search
CPC ........ G16H 20/40; G16H 50/50; A61C 13/34; A61C 19/00; A61C 19/04; A61C 19/05; A61C 9/0046; A61C 11/00
See application file for complete search history.

(56) References Cited

U.S. PATENT DOCUMENTS 7,837,469 B2    11/2010    Chishti et al.
8,126,726 B2    2/2012    Matov et al.
(Continued)

FOREIGN PATENT DOCUMENTS

WO    2018035524 A1    2/2018

OTHER PUBLICATIONS

Allied Market Research—Jun. 5, 2019 https://www.prnewswire.com/news-releases/global-preoperative-surgical-planning-software-market-to-reach-126-81-million-globally-by-2026-at-5-2-cagr-amr-300862389.html.
(Continued)

*Primary Examiner* — Vijay Shankar
(74) *Attorney, Agent, or Firm* — Meunier Carlin & Curfman LLC

(57) ABSTRACT

Methods and systems for establishing dental occlusion are described herein. These systems and methods can be used for 1-, 2-, or 3-piece maxillary orthognathic surgeries. An example computer-implemented method includes receiving a maxillary dental model and a mandibular dental model, identifying a plurality of dental landmarks in each of the maxillary and mandibular dental models, and extracting a plurality of points-of-interest from each of the maxillary and mandibular dental models. The dental landmarks include a plurality of maxillary dental landmarks and a plurality of
(Continued)

mandibular dental landmarks. The method further includes aligning the maxillary and mandibular points-of-interest, and fine tuning the alignment of the maxillary and mandibular dental models to achieve maximum contact with a collision constraint.

22 Claims, 21 Drawing Sheets

(56) References Cited

U.S. PATENT DOCUMENTS

| | | | |
|---|---|---|---|
| 8,425,229 | B2 | 4/2013 | Nilsson et al. |
| 10,304,190 | B2 | 5/2019 | Alvarez et al. |
| 10,307,229 | B2 | 6/2019 | Hauth et al. |
| 10,335,251 | B2 * | 7/2019 | See ................. A61C 7/002 |
| 10,945,818 | B1 * | 3/2021 | Motlagh ............. A61C 7/08 |
| 11,523,886 | B2 * | 12/2022 | Xia ................. A61C 13/0004 |
| 11,793,605 | B2 * | 10/2023 | Aptekarev ........... G16H 20/30 |
| 11,833,008 | B1 * | 12/2023 | Motlagh ............. A61F 5/566 |
| 11,963,832 | B2 * | 4/2024 | Xia ................. A61C 7/002 |
| 2017/0128161 | A1 | 5/2017 | See et al. |
| 2020/0197137 | A1 * | 6/2020 | Xia ................. A61C 13/0004 |
| 2023/0111070 | A1 * | 4/2023 | Xia ................. G06T 7/0014 382/128 |

OTHER PUBLICATIONS

Bland, and D. Altman, "Statistical methods for assessing agreement between two methods of clinical measurement," Lancet, vol. 327, No. 8476, pp. 307-310, 1986.

Chabanas, "Models for Planning and Simulation in Computer Assisted Orthognatic Surgery," in Proceedings of the 5th International Conference on Medical Image Computing and Computer-Assisted Intervention—Part II, 2002, pp. 315-322.

Chang, Y.-B., et al., An automatic and robust algorithm of reestablishment of digital dental occlusion. IEEE transactions on medical imaging, 2010. 29(9): p. 1652-1663.

Chang, Y.-B., et al., In vitro evaluation of new approach to digital dental model articulation. Journal of oral and maxillofacial surgery : official journal of the American Association of Oral and Maxillofacial Surgeons, 2012. 70(4): p. 952-962.

Deng, H., Yuan, P., Wong, S. et al. An automatic approach to establish clinically desired final dental occlusion for one-piece maxillary orthognathic surgery. Int J Cars 15, 1763-1773 (2020). https://doi.org/10.1007/s11548-020-02125-y.

Deng, P. Yuan, S. Wong, J. Gateno, F. A. Garrett, R. K. Ellis, J. D. English, H. B. Jacob, D. Kim, J. C. Barber, W. Chen, and J. Xia, "An Automatic Approach to Reestablish Final Dental Occlusion for 1-Piece Maxillary Orthognathic Surgery," in Medical Image Computing and Computer-Assisted Intervention—MICCAI 2019, Shenzhen, China.

Hao Wang, and Z. Li, "Tooth separation from dental model using segmentation field," in 2016 38th Annual International Conference of the IEEE Engineering in Medicine and Biology Society (EMBC), 2016, pp. 5616-5619.

Ho CT, Lin HH, Lo LJ: Intraoral scanning and setting up the digital final occlusion in three-dimensional planning of orthognathic surgery: Its comparison with the dental model approach. Plast Reconstr Surg 143:1027e, 2019.

Kumar, R. Janardan, and B. Larson, "Automatic Feature Identification in Dental Meshes," Computer-Aided Design and Applications, vol. 9, No. 6, pp. 747-769, Jan. 1, 2012, 2012.

Kumar, R. Janardan, B. Larson, and J. Moon, "Improved Segmentation of Teeth in Dental Models," Computer-Aided Design and Applications, vol. 8, Jan. 1, 2011.

Li, J., et al., New approach to establish an object reference frame for dental arch in computeraided surgical simulation. International journal of oral and maxillofacial surgery, 2017. 46(9): p. 1193-1200.

Liao, S.-j. Liu, B.-j. Zou, X. Ding, Y. Liang, and J.-h. Huang, "Automatic Tooth Segmentation of Dental Mesh Based on Harmonic Fields," BioMed Research International, vol. 2015, pp. 10, 2015:187173.

Lu, J. Yang, W. Wang, Z. Li, and Z. Lu, "Teeth Classification Based on Extreme Learning Machine," in 2018 Second World Conference on Smart Trends in Systems, Security and Sustainability (WorldS4), 2018, pp. 198-202.

Ma, and Z. Li, "Computer aided orthodontics treatment by virtual segmentation and adjustment," in 2010 International Conference on Image Analysis and Signal Processing, 2010, pp. 336-339.

Mouritsen, "Automatic Segmentation of Teeth in Digital Dental Models": University of Alabama at Birmingham, Graduate School, 2013.

Nadjmi, N., et al., Virtual occlusion in planning orthognathic surgical procedures. International Journal of Oral & Maxillofacial Surgery, 2010. 39(5): p. 457-462.

Sheng-Pin Hsu S, Gateno J, Bell R, et al. Accuracy of a Computer-Aided Surgical Simulation Protocol for Orthognathic Surgery: A Prospective Multicenter Study. Journal of oral and maxillofacial surgery: official journal of the American Association of Oral and Maxillofacial Surgeons. Jun. 11, 2012;71(1): 128-142.

Sinthanayothin, and W. Tharanont, "Orthodontics treatment simulation by teeth segmentation and setup," in 2008 5th International Conference on Electrical Engineering/Electronics, Computer, Telecommunications and Information Technology, 2008, pp. 81-84.

Späth C, Kordass B, Optimization of the static occlusion by "occlusal surface settling" in the Cerec 3D software. International Journal of Computerized Dentistry Apr. 2006, 9(2):121-1. (PMID: 16955649).

Wu, L. Chen, J. Li, and Y. Zhou, "Tooth segmentation on dental meshes using morphologic skeleton," Computers & Graphics, vol. 38, pp. 199-211, 2014.

Wu, W., et al., Haptic simulation framework for determining virtual dental occlusion. International Journal of Computer Assisted Radiology and Surgery, 2017. 12(4): p. 595-606.

Xia JJ, Gateno J, Teichgraeber JF, et al. Accuracy of the Computer-Aided Surgical Simulation (CASS) System in the Treatment of Patients With Complex Craniomaxillofacial Deformity: A Pilot Study. Journal of Oral and Maxillofacial Surgery. Feb. 1, 2007 2007;65(2):248-254.

Xia, J.J., et al. Automated Digital Dental Articulation. in Medical Image Computing and Computer-Assisted Intervention—MICCAI 2010. 2010. Berlin, Heidelberg: Springer Berlin Heidelberg.

Xia, J.J., et al., Algorithm for planning a double-jaw orthognathic surgery using a computeraided surgical simulation (CASS) protocol. Part 1: planning sequence. International journal of oral and maxillofacial surgery, 2015. 44(12): p. 1431-1440.

Xia, J.J., et al., Algorithm for planning a double-jaw orthognathic surgery using a computeraided surgical simulation (CASS) protocol. Part 2: three-dimensional cephalometry. International Journal of Oral & Maxillofacial Surgery, 2015. 44(12): p. 1441-1450.

Xia, Y.-B. Chang, J. Gateno, Z. Xiong, and X. Zhou, "Automated Digital Dental Articulation," in Medical Image Computing and Computer-Assisted Intervention—MICCAI 2010, Berlin, Heidelberg, 2010, pp. 278-286.

Yuan P, Mai H, Li J, et al. Design, development and clinical validation of computer-aided surgical simulation system for streamlined orthognathic surgical planning. International Journal of Computer Assisted Radiology and Surgery. Apr. 21, 2017;12.

Zou, S.-J. Liu, S.-H. Liao, X. Ding, and Y. Liang, "Interactive tooth partition of dental mesh base on tooth-target harmonic field," Computers in biology and medicine, vol. 56C, pp. 132-144, Nov. 13, 2014.

International Search Report and Written Opinion mailed Jan. 29, 2021, from International Application No. PCT/US2020/055263, 8 pages.

\* cited by examiner

| Description | Abbreviation |
|---|---|
| *Upper* | |
| Midpoint of the right and left central incisal edges | U0 |
| Canine cusp[a] | U3C |
| Mesiobuccal cusp of the 1st molar[a] | U6MBC |
| Mesiobuccal cusp of the 2nd molar[a] | U7MBC |
| *Lower* | |
| Midpoint of the right and left central incisal edges | L0 |
| Canine cusp[a] | L3C |
| Mesiobuccal cusp of the 1st molar[a] | L6MBC |
| Mesiobuccal cusp of the 2nd molar[a] | L7MBC |

[a]Bilateral landmark

FIG. 11

| Description | Abbreviation |
|---|---|
| *Upper* | |
| Mesiolingual cusp of the 1st molar[a] | U6MLC |
| Central fossa of the 1st molar[a] | U6CF |
| *Lower* | |
| Embrasure between canine and the 1st premolar[a] | L34Embr |
| Distobuccal cusp of the 1st molar[a] | L6DBC |
| Central fossa of the 1st molar[a] | L6CF |

[a]Bilateral landmark

FIG. 12

|          | Landmarks |         |        |        |
|----------|-----------|---------|--------|--------|
| Upper    | U0        | U3C[a]  | U6MLC[a] | U6CF[a] |
| Paired lower | L0    | L34Embr[a] | L6CF[a] | L6DBC[a] |

[a]Bilateral landmark

| Measurement | Algorithm | Abbreviation |
|---|---|---|
| Midline | -0.16 | 0.06 |
| Canine (R) | 1.44 | 1.23 |
| Canine (L) | -0.73 | -0.83 |
| Molar (R) | 2.10 | 2.03 |
| Molar (L) | 2.36 | 2.48 |

FIG. 20

| Measurement | Mean | STD | Lower limit | Upper limit |
|---|---|---|---|---|
| U0 | -0.22 | 0.37 | -0.94 | 0.51 |
| CR | 0.21 | 0.47 | -0.72 | 1.14 |
| CL | 0.1 | 0.57 | -1.02 | 1.22 |
| MR | 0.07 | 0.61 | -1.12 | 1.25 |
| ML | -0.12 | 0.61 | -1.31 | 1.07 |

FIG. 21

| Landmark Name | Description |
|---|---|
| U0* | Central upper dental midline, located between upper right and left central incisal edges |
| U3Cusp-R, U3Cusp-L* | Cusp of the upper canine, right or left |
| U6MPCusp-R, U6MPCusp-L† | Mesiopalatal cusp of upper first molar, right or left |
| L0* | Central lower dental midline, located between lower right and left central incisal edges |
| L34Embr-R, L34Embr-L† | Embrasure between lower canine and first premolar, right or left |
| L6CF-R, L6CF-L† | Central fossa of lower first molar, right or left |

*Landmarks routinely used during surgical planning (manually digitized by the planner).
† Landmarks not routinely used during surgical planning (automatically extracted by our approach).

FIG. 22

| Relationship | Paired Landmarks | |
|---|---|---|
| | Upper | Lower |
| Midline | U0 | L0 |
| Right canine | U3Cusp-R | L34Embr-R |
| Left canine | U3Cusp-L | L34Embr-L |
| Right first molar | U6MPCusp-R | L6CF-R |
| Left first molar | U6MPCusp-L | L6CF-L |

FIG. 23

| Relationship | Measurement (mm) |
|---|---|
| Midline | |
| Mediolateral (x-axis) | 0.2 ± 0.3 |
| Buccolingual (y-axis) | 0.0 ± 0.5 |
| Superoinferior (z-axis) | 0.0 ± 0.4 |
| Right canine | |
| Mesiodistal (x-axis) | 0.1 ± 0.5 |
| Buccolingual (y-axis) | 0.1 ± 0.5 |
| Superoinferior (z-axis) | 0.0 ± 0.3 |
| Left canine | |
| Mesiodistal (x-axis) | 0.1 ± 0.5 |
| Buccolingual (y-axis) | 0.1 ± 0.5 |
| Superoinferior (z-axis) | 0.0 ± 0.4 |
| Right Molar | |
| Mesiodistal (x-axis) | 0.0 ± 0.4 |
| Buccolingual (y-axis) | 0.2 ± 0.6 |
| Superoinferior (z-axis) | 0.1 ± 0.3 |
| Left Molar | |
| Mesiodistal (x-axis) | 0.1 ± 0.5 |
| Buccolingual (y-axis) | 0.2 ± 0.5 |
| Superoinferior (z-axis) | 0.0 ± 0.2 |

Data presented as mean ± standard deviation.

FIG. 25

AUTOMATIC APPROACH TO ESTABLISH DENTAL OCCLUSION FOR 1-PIECE, 2-PIECE, AND 3-PIECE MAXILLARY ORTHOGNATHIC SURGERIES

CROSS-REFERENCE TO RELATED APPLICATIONS

This application is a United States National Stage Patent Application filed under 35 U.S.C. § 371 of International Patent Application Number PCT/US2020/055263, filed on Oct. 12, 2020, which claims the benefit of U.S. provisional patent application No. 62/913,393, filed on Oct. 10, 2019, and entitled "An Automatic Approach to Reestablish Optimal Dental Occlusion for 1-Piece, 2-Piece and 3-Piece Maxillary Orthognathic Surgeries," the disclosures of which are expressly incorporated herein by reference their entirety.

STATEMENT REGARDING FEDERALLY FUNDED RESEARCH

This invention was made with government support under Grant no. RO1 DE022676 awarded by the National Institutes of Health/National Institute of Dental and Craniofacial Research. The government has certain rights in the invention.

BACKGROUND

Orthognathic surgery emerged as a technical procedure to correct dento-skeletal deformities, correcting both esthetical and functional alterations which include occlusal, respiratory and articular abnormalities. In the last decade, computer-aided surgical simulation (CASS) has become the standard of care for planning orthognathic surgery. An important step in CASS planning orthognathic surgery is to establish a desired dental occlusion (called "final occlusion") between the upper and lower teeth. Traditionally, surgeons hand-articulate upper and lower stone dental models as the instant tactile response and cognitive insight help them to quickly achieve a desired position of the stone models, e.g., midline alignment, Class I canine and molar relations, and a maximized contact between the upper and lower teeth.

However, several digital challenges exist in that the digital upper and lower dental models represented by point clouds or triangulated surfaces have a lack of tactile response. When they are in contact, the models can still be moved digitally towards and penetrate into each other. Therefore, in the current CASS clinical protocol, surgeons still need to hand-articulate the stone models to the final occlusion and scan them together into the computer. This process is convoluted, time-consuming and cost-inefficient, and may introduce unpredicted inaccuracy into the planning.

Software exists on the market purporting to determine digital dental occlusion. However, such software either require moving the models together manually or are computationally inefficient and thus have not been used clinically. A method of digitally articulating the upper and lower dental models into maximum intercuspation (MI) has also been developed. However, this method is problematic and only used in the laboratory setting. For example, this method only considers MI relationship, which is an occlusion that simply maximizes the contacting areas between the upper and lower teeth without considering the other important clinical criteria. Thus, the results are not applicable to the clinic. In addition, the braces and the gums must be manually extracted from the digital models in this method. Moreover, this method is computationally inefficient as even after the models are manually prepared, it takes more than an hour to complete the computation.

SUMMARY

Described herein are methods and systems for automatically establishing dental occlusion. The described systems and methods provide a fully-automated technique for digital dental articulation of upper and lower dental models.

An example algorithm includes a three-stage approach to automatically articulate the upper and lower dental models to the final occlusion for 1-piece maxillary orthognathic surgery. In the first stage, points of interest (POI) and four key teeth landmarks are automatically extracted from the teeth occlusal surfaces. In the second stage, the upper and lower teeth are aligned to a clinically desired Midline-Canine-Molar (M-C-M) relationship. In the third stage, the upper and lower teeth are finely aligned to a best possible maximum contact.

An example computer-implemented method for establishing dental occlusion is described herein. The method includes receiving a maxillary dental model and a mandibular dental model; and identifying a plurality of dental landmarks in each of the maxillary and mandibular dental models, where the dental landmarks includes a plurality of maxillary dental landmarks and a plurality of mandibular dental landmarks. The method also includes extracting a plurality of points-of-interest from each of the maxillary and mandibular dental models; aligning the maxillary and mandibular dental models; and fine tuning the alignment of the maxillary and mandibular dental models to achieve maximum contact with a collision constraint.

In some implementations, the method includes adjusting the alignment of the maxillary and mandibular dental models based on user input.

In some implementations, the points-of-interest extracted from each of the maxillary and mandibular dental models are on respective occlusal surfaces of the maxillary and mandibular dental models.

In some implementations, the step of extracting a plurality of points-of-interest from each of the maxillary and mandibular dental models further includes extracting respective maxillary and mandibular occlusal surface models from each of the maxillary and mandibular dental models; extracting the points-of-interest from the respective maxillary and mandibular occlusal surface models; and classifying a plurality of convex and concave points from among the points-of-interest. Optionally, the method further includes identifying, using the convex points, a plurality of cusps on each of the respective maxillary and mandibular occlusal surface models; and identifying, using the concave points, a central groove in at least one of the respective maxillary and mandibular occlusal surface models.

In some implementations, the dental landmarks include at least one of a midpoint between central incisors, a cusp point, a groove point, or an embrasure between teeth. Optionally, the step of identifying a plurality of dental landmarks in each of the maxillary and mandibular dental models includes receiving a location of at least one of the dental landmarks from a user. Optionally, the step of identifying a plurality of dental landmarks in each of the maxillary and mandibular dental models includes detecting a location of at least one of the dental landmarks.

In some implementations, the step of aligning the maxillary and mandibular dental models includes aligning a midline pair and at least one canine or embrasure pair of the maxillary and mandibular dental landmarks along a tangent line of a dental arch, and minimizing a sum of distances between at least one pair of the maxillary and mandibular dental landmarks. The at least one pair of the maxillary and mandibular dental landmarks includes at least one molar pair of the maxillary and mandibular dental landmarks.

In some implementations, the step of aligning the maxillary and mandibular dental models includes aligning an upper dental curve and a lower dental curve. For example, the method further includes extracting the upper and lower dental curves from the maxillary and mandibular dental models, respectively; estimating a respective frame of reference for each of the upper and lower dental curves; and aligning the respective frames of references of the upper and lower dental curves after registering a midline pair of the maxillary and mandibular dental landmarks.

In some implementations, the maxillary dental model includes a plurality of individual segments.

For example, in some implementations, the individual segments may be a major segment and a minor segment, and the step of aligning the maxillary and mandibular dental models includes aligning the major segment of the maxillary dental model and the mandibular dental model by aligning a midline pair and at least one canine or embrasure pair of the maxillary and mandibular dental landmarks along a tangent line of a dental arch, and by minimizing a sum of distances between at least one molar pair of the maxillary and mandibular dental landmarks; and aligning the minor segment of the maxillary dental model and the mandibular dental model by aligning an embrasure between teeth of the major and minor segments of the maxillary dental model and at least one canine, premolar or embrasure pair of the maxillary and mandibular dental landmarks along the tangent line of the dental arch, and by minimizing a sum of distances between at least one molar pair of the maxillary and mandibular dental landmarks.

In other implementations, the individual segments may be a right segment and a left segment, and the step of aligning the maxillary and mandibular dental models includes aligning a right segment of the maxillary dental model and the mandibular dental model by aligning a midline pair and at least one canine or embrasure pair of the maxillary and mandibular dental landmarks along a tangent line of a dental arch, and by minimizing a sum of distances at least one molar pair of the maxillary and mandibular dental landmarks; and aligning a left segment of the maxillary dental model and the mandibular dental model by aligning a midline pair and at least one canine or embrasure pair of maxillary and mandibular dental landmarks along the tangent line of the dental arch, and by minimizing a sum of distances between at least one molar pair of the maxillary and mandibular dental landmarks.

Optionally, the method further includes comparing respective curves of Wilson of the aligned maxillary and mandibular dental models.

In yet other implementations, the individual segments include an anterior segment and left and right posterior segments. The method further includes receiving an overbite; and receiving an overjet, and the step of aligning the maxillary and mandibular dental models includes aligning the maxillary and mandibular dental models by aligning a midline pair of the maxillary and mandibular dental landmarks along a tangent line of a dental arch, by considering a curvature of the anterior segment of the maxillary dental model to a curvature of the mandibular dental model, and by minimizing a sum of distances between at least one pair of the points-of-interests of the maxillary and mandibular incisors; and aligning each of the left and right posterior segments of the maxillary dental model and the mandibular dental model by aligning an embrasure between teeth of the anterior and posterior segments of the maxillary dental model and at least one canine, premolar, or embrasure pair of the maxillary and mandibular dental landmarks along the tangent line of the dental arch, and by minimizing a sum of distances between at least one molar pair of the maxillary and mandibular dental landmarks.

Optionally, the method further includes iteratively aligning the maxillary and mandibular dental models for each of a plurality of overbites and/or overjets. Additionally, the method optionally further includes ranking the iteratively aligned maxillary and mandibular dental models.

Optionally, the method further includes comparing respective curves of Wilson of the aligned maxillary and mandibular dental models.

In some implementations, the aligned maxillary and mandibular dental models represent a dental occlusion. In some implementations, the aligned maxillary and mandibular dental models represent an optimal position for a next stage of orthodontic treatment.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 4A illustrates major and minor segments of the maxillary model. FIG. 4B illustrates left and right segments of the maxillary model.

FIG. 6A illustrates anterior, right posterior, and left posterior segments of the maxillary model. FIG. 6B illustrates anterior, right posterior, and left posterior segments of the maxillary model in relation to the mandibular model.

FIG. 9A shows midline alignment. FIG. 9B shows Class I relationship. FIG. 9C shows molar cusp-fossa relationship with maximum contact.

FIG. 11 is Table 1, which shows clinically digitized teeth landmarks.

FIG. 12 is Table 2, which shows automatically detected teeth landmarks.

FIG. 13A shows upper teeth landmarks. FIG. 13B shows lower teeth landmarks.

FIG. 14A shows the fitting curve. FIG. 14B shows the extracted occlusal surface. FIG. 14C shows the intersection plane and envelope.

FIG. 15A shows detection of the most prominent peak point. FIG. 15B shows envelop simplification. FIG. 15C shows a concave separation point. FIG. 15D shows detection of second peak point.

FIG. 16A is the upper (maxillary teeth) model. FIG. 16B is the lower (mandibular teeth) model.

FIG. 20 is Table 4, which shows mean distance comparison (millimeters (mm)).

FIG. 21 is Table 5, which shows Bland and Altman's measurement (mm).

FIG. 22 is Table 6, which shows teeth landmarks used in digital dental articulation.

FIG. 23 is Table 7, which shows paired landmarks used in the measurements.

FIG. 25 is Table 8, which shows descriptive results (differences between the two articulation methods in mm).

DETAILED DESCRIPTION

Figure 1:
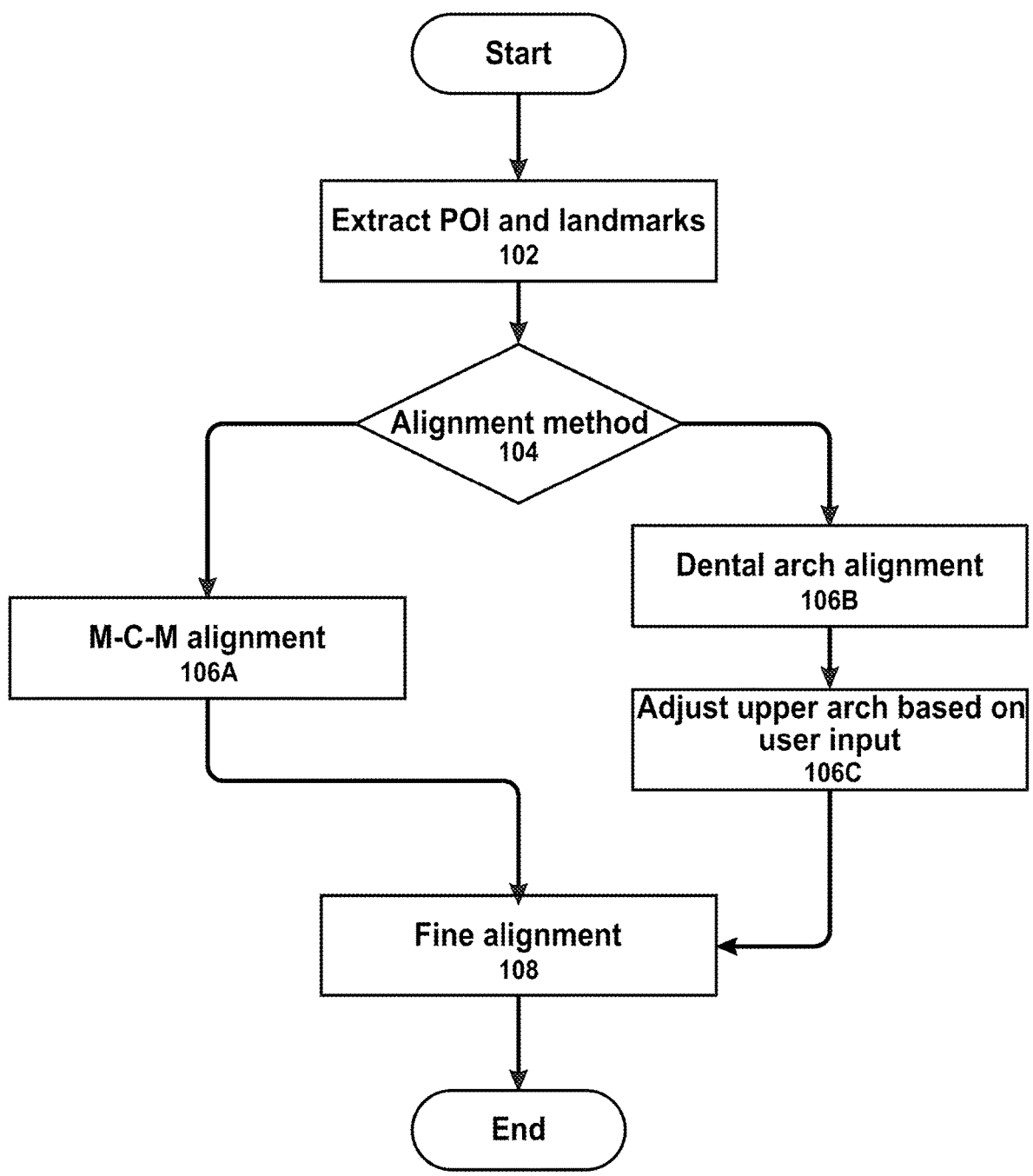
FIG. 1 is a flowchart illustrating example operations for establishing dental occlusion for 1-piece maxillary orthognathic surgeries according to an implementation described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Described herein are methods and systems for automatically establishing dental occlusion. The described systems and methods provide a fully automatic technique for digital dental articulation of upper and lower dental models. Such a fully-automated technique is not conventionally available. Instead, in conventional protocols for virtual surgical planning, stone models are first manually articulated to the final occlusion and then scanned together using a cone-beam computed tomography (CBCT) scanner or a surface scanner. The resultant digital teeth model serves as the template for articulating the upper and lower dental models to the final occlusion during surgical planning. This process is both time-consuming and cost-inefficient. Additionally, when an intraoral scanner is used, the upper and lower digital dental models are often printed using a three-dimensional (3D) printer for manual articulation. This completely defeats the purpose of using an intraoral scanner. The clinical benefits of the methods and systems described herein are therefore significant. First, it allows doctors to eliminate the need to articulate stone dental models of the patient's dentition (or in some cases the use of stone dental models altogether). Additionally, it allows doctors to obtain a clinically desired final occlusion digitally that is equally as good as the hand-articulated result, and this can be accomplished in quickly (e.g., within minutes). Further, the methods and systems described herein overcome technical challenges present in conventional virtual surgical planning systems. For example, the methods and systems described herein prevent 3D models (which consist of points and rendered surfaces) from penetrating one another as a result of digital articulation. The methods and systems described herein also constrain the alignment based on clinical criteria and/or anatomical considerations. The methods and systems described herein also allow for braces and/or gingiva to be removed from the models prior to digital articulation.

Figure 2:
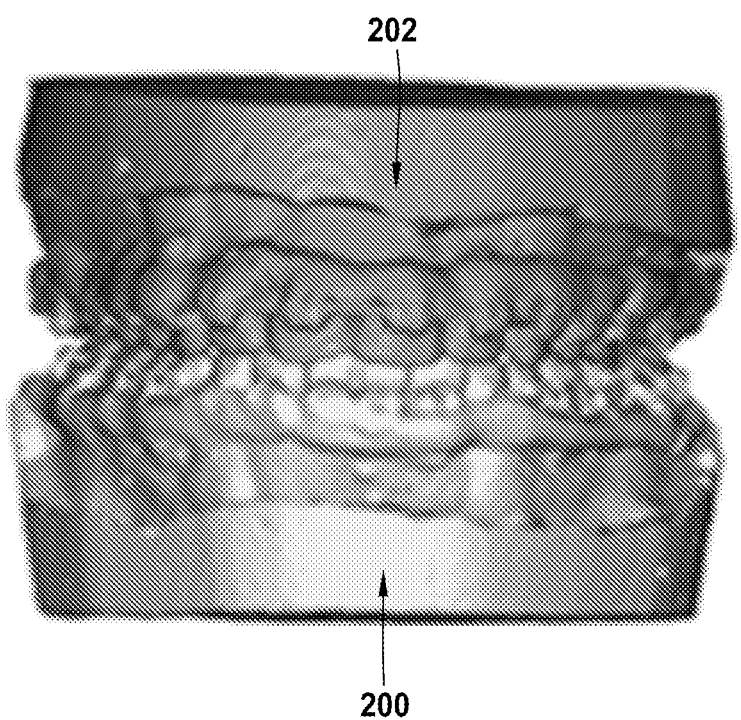
FIG. 2 illustrates example maxillary and mandibular models for 1-piece maxillary orthognathic surgeries according to an implementation described herein.

Referring now to FIG. 1, an example method for establishing dental occlusion for 1-piece maxillary orthognathic surgeries is described. This disclosure contemplates that the operations described herein can be implemented by a computing device (e.g., computing device 800 shown in FIG. 8). The method for establishing dental occlusion operates on three-dimensional (3D) models such as standard tessellation language (STL) files. The 3D models may include bone, teeth, gingiva parts, and even orthodontic devices (e.g., braces). STL file format is provided only as an example 3D model file type. This disclosure contemplates that other file formats may be used with the techniques described herein. The 3D models described herein can be generated from medical images. Such 3D images capture both a patient's 3D soft tissue surfaces, 3D bone structure, and if applicable orthodontic devices such as braces. The 3D images can be obtained by scanning stone dental models of the patient's dentition using cone-beam computed tomography (CBCT) or a 3D surface scanner. Alternatively, the 3D images can be obtained by scanning the patient's teeth using an intraoral scanner. It should be understood that CBCT, 3D surface scanners, and intraoral scanners are provided only as example imaging systems for obtaining 3D images and that other imaging modalities may be used to capture the 3D images. 3D images including medical images (e.g., Digital Imaging and Communication in Medicine (DICOM) files) can be converted into 3D models, for example, using computer-aided design (CAD) software. Thus, the maxillary and mandibular models described herein may be 3D models generated from 3D images. FIG. 2 illustrates an example mandibular dental model 200 and maxillary dental model 202. For 1-piece maxillary orthognathic surgeries, the maxillary dental model 202 remains intact. This is in contrast to 2-piece and 3-piece maxillary orthognathic surgeries as described below, where the maxillary dental model includes a plurality of segments (see e.g., FIGS. 4A-4B and 6A-6B).

Referring again to FIG. 1, a plurality of points-of-interest (POI) and a plurality of dental landmarks are extracted from each of the maxillary and mandibular dental models (see e.g., models shown in FIG. 2) at step 102. As described in detail herein, the extracted POI (or point clouds) from each of the dental models are on the respective occlusal surfaces of the models. The extracted POI (e.g., thousands of points) form the edges, cusps, and grooves of the upper and lower teeth. The POI are extracted from maxillary and mandibular occlusal surface models. In addition to POI, dental landmarks are also extracted from the each of the maxillary and mandibular dental models. As described in detail herein, the extracted dental landmarks include those that are not routinely digitized for surgical planning. Dental landmarks can be identified by a user (FIG. 11, Table 1) and/or automatically detected (FIG. 12, Table 2) as described herein.

At step 104, an alignment method is selected. In the 1-piece surgery examples described herein, the lower teeth model (or "mandibular dental model") remains static, while the upper dental model (or "maxillary dental model") is translationally and rotationally transformed and articulated to the lower teeth model. It should be understood that in other implementations for 1-piece surgery the upper dental model (or "maxillary dental model") may remain static, while the lower teeth model (or "mandibular dental model") is translationally and rotationally transformed and articulated to the upper teeth model. In some cases, the upper dental arch (which is represented by the maxillary dental model and/or extracted POI) is articulated relative to the lower dental arch (which is represented by the mandibular dental model and/or extracted POI) according to the midline-canine-molar (M-C-M) relationship. This is shown by step 106A. Optionally, the method of 106A is used for cases where the upper and lower dental arches are well aligned and/or in cases where the patient is missing one or more teeth that are not involved in or changing M-C-M relationship. In other cases, the upper dental arch (which is represented by the maxillary dental model and/or extracted POI) is articulated relative to the lower dental arch (which is represented by the mandibular dental model and/or extracted POI) according to the respective dental curves of upper and lower dental arches. This is shown by step 106B. Optionally, the method of 106B is used for cases where the upper and lower dental arches are not well aligned and/or in cases where the patient is missing one or more teeth involved in or changing the M-C-M relationship. The respective dental curves of the upper and lower dental arches can be obtained by first fitting a curve to the respective dental landmarks of the maxillary and mandibular dental models. An optimal object reference frame for each dental curve can then be estimated. For example, principal component analysis-based adaptive minimum Euclidean distances (PAMED) method as described in Li, J. et al., New approach to establish an object reference frame for dental arch in computer-aided surgical simulation. Int J Oral Maxillofac Surg. 2017; 46 (9):1193-1200 can be used to estimate an optimal object reference frame for each dental curve. It should be understood that the PAMED method is provided only as an example and that other techniques for establishing a reference frame may be used. The reference frames of the maxillary and mandibular dental models can then be aligned together after the midpoints between the right and left central incisor of the upper and lower dental curves, i.e., U0 and L0, are perfectly registered together. Optionally, at step 106C, the maxillary dental model is adjusted based on a user's input. This includes, but is not limited to, adjustments made based on a surgeon's experience and/or assessment. For example, in case the presurgical orthodontics is not completed due to the clinical reason, if needed, a surgeon can manually fine tune the overbite and overjet of upper dental arch based on experience and assessment.

At step 108, the alignment of the upper and lower dental arches is fine tuned. For example, the upper dental arch is adjusted to achieve the maximum contact with the collision constraint. This ensures that the upper and lower dental arch models do not penetrate one another as a result of the alignment performed at step 106A or 106B. The previously established M-C-M relationship (step 106A) or dental curve relationship (step 106B) is maintained during the fine alignment of step 108.

Figure 3:
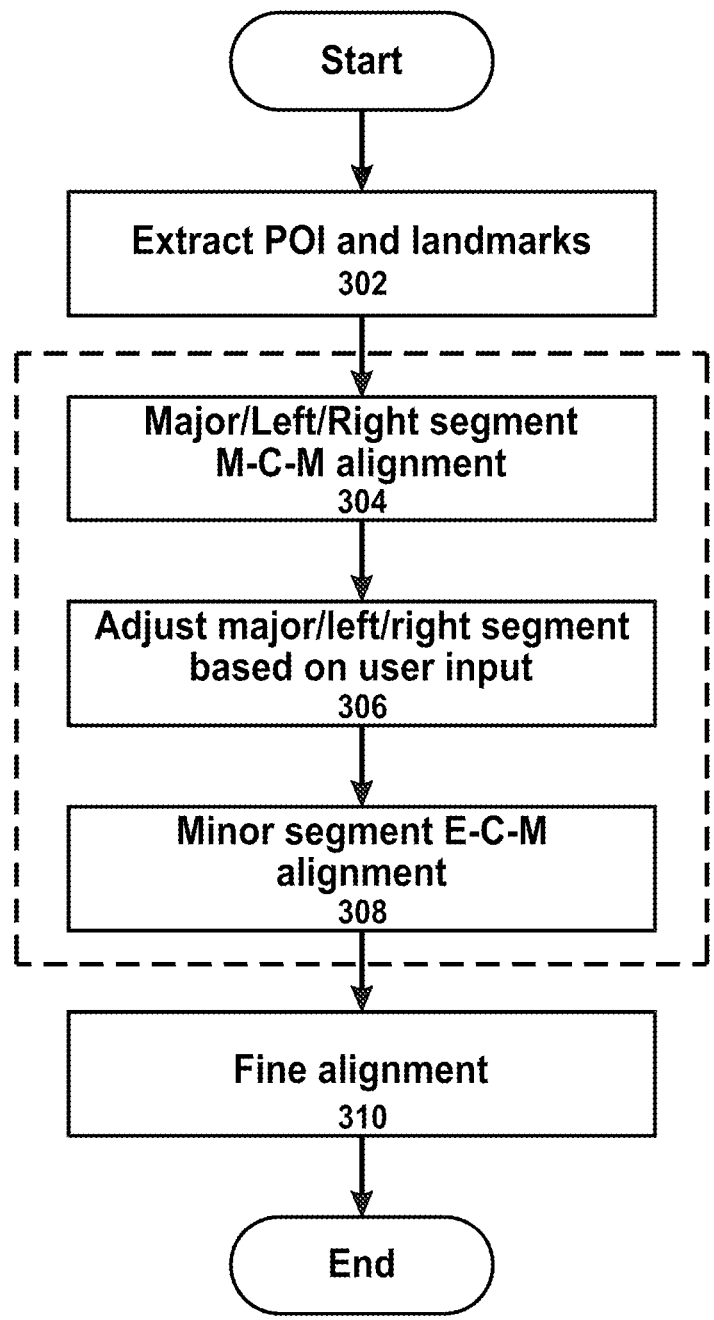
FIG. 3 is a flowchart illustrating example operations for establishing dental occlusion for 2-piece maxillary orthognathic surgeries according to an implementation described herein.
Figure 4A:
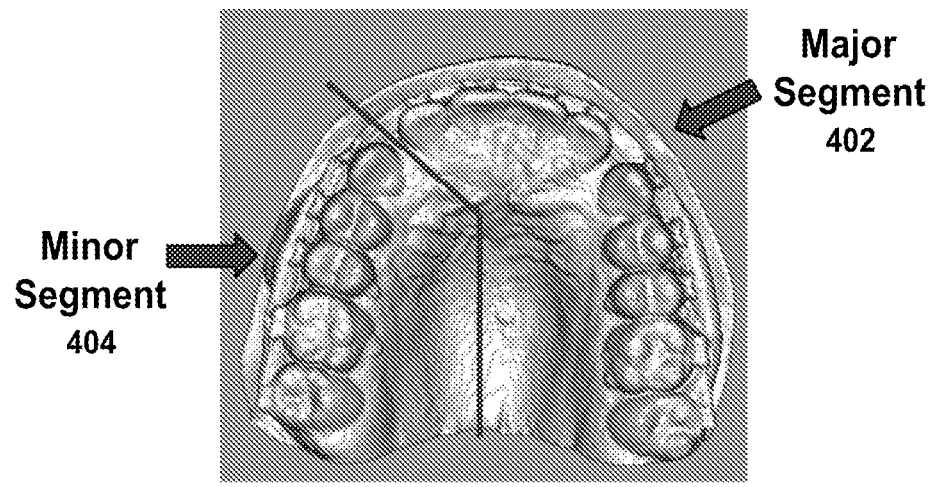
FIGS. 4A-4B illustrate example maxillary models for 2-piece maxillary orthognathic surgeries according to an implementation described herein.
Figure 4B:
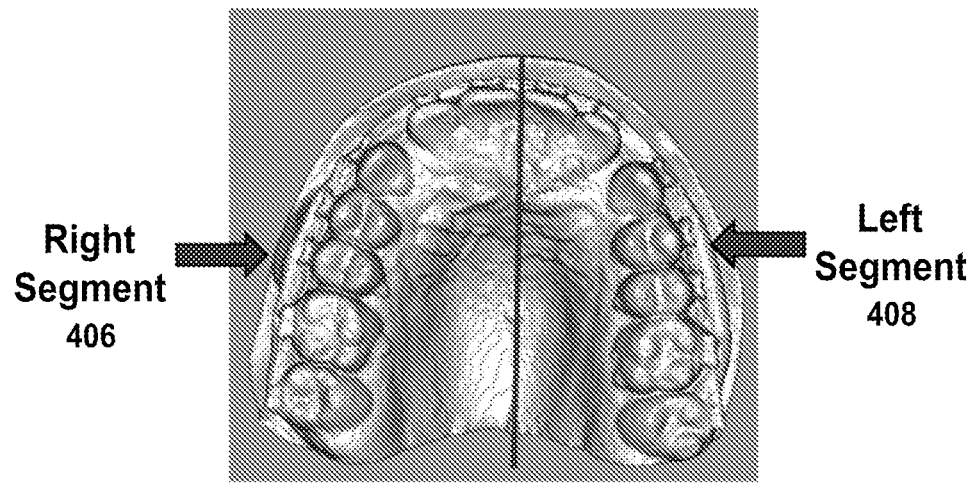

Referring now to FIG. 3, an example method for establishing dental occlusion for 2-piece maxillary orthognathic surgeries is described. This disclosure contemplates that the operations described herein can be implemented by a computing device (e.g., computing device 800 shown in FIG. 8). As described above, the method for establishing dental occlusion operates on 3D models generated from 3D images acquired by a scanner, e.g., CBCT or 3D surface/intraoral scanner. As shown in FIGS. 4A-4B, the maxillary dental model includes two pieces or segments. FIG. 4A illustrates the major segment 402 and minor segment 404 of the maxillary dental model. In this case, the maxillary dental models includes two asymmetrical segments. FIG. 4B illustrates the right segment 406 and left segment 408 of the maxillary dental model. In this case, the maxillary dental model is split in the middle between the right and left central incisors. Although not shown in FIGS. 4A-4B, the segments shown in FIGS. 4A-4B are articulated relative to a mandibular dental model. For 2-piece surgeries, the lower teeth model (or "mandibular dental model") remains static, while each piece of the upper dental model (or "maxillary dental model") is translationally and rotationally transformed and articulated to the lower teeth model.

Referring again to FIG. 3, a POI and a plurality of dental landmarks are extracted from each of the maxillary and mandibular dental models (see e.g., models shown in FIGS. 4A-4B) at step 302. POI and dental landmark extraction is described above with regard to step 102 of FIG. 1 and is therefore not described in further detail below.

At step 304, the major/right/left segment of the maxillary model is articulated relative to the mandibular model according to the M-C-M relationship. For this step, the midpoint of the central incisors, canine and molar on the articulated segment are used. It should be understood that for cases of right-left segmentation (see FIG. 4B), each of the right segment and left segment is articulated separately at step 304. Optionally, at step 306, the major/right/left segment of the maxillary model is adjusted based on a user's input. This includes, but is not limited to, adjustments made based on a surgeon's experience and/or assessment (e.g., overbite, overjet).

At step 308, the minor segment of the maxillary model is articulated relative to the mandibular model according to the embrasure-canine-molar (E-C-M) relationship. The E-C-M relationship considers the upper teeth embrasure between lateral incisor and canine, the Class I canine and Class I molar relationship. It should be understood that for cases of right-left segmentation (see FIG. 4B), step 308 is not performed (i.e., there is no minor segment). Additionally, it should be understood that the steps of FIG. 3 shown in the dotted box achieve the alignment accomplished by step 106A of FIG. 1 for 1-piece maxillary orthognathic surgeries.

At step 310, the alignment of the maxillary and mandibular models is fine tuned. For example, each of the major/minor or right/left segments of the maxillary model are adjusted to achieve the maximum contact with the collision constraint. This ensures that the maxillary and mandibular models do not penetrate one another as a result of the alignment performed at step 304 and 308. The previously established M-C-M relationship (step 304) and/or E-C-M relationship (step 308) is maintained during the fine alignment of step 310.

Optionally, the alignment of the maxillary and mandibular models can be constrained by the distance between the individual segments (e.g., major/minor or left/right). The individual segments should not get too close (i.e., to avoid collisions between the bones). As described above, 3D models (which are formed of points and rendered surfaces) can penetrate each other as a result of digital articulation. Additionally, the gap between the individual segments (e.g., major/minor or left/right) should be less than the limit of mucosa stretch, which is about 5 mm, which is an anatomical constraint. Such constraints can be accomplished by limiting the distance between the cutting surfaces of the individual segments. Also curves of Wilson of the aligned maxillary and mandibular models should be maintained. It should be understood that the curve of Wilson is the upward U-shaped curvature of the maxillary and mandibular occlusal planes. When viewed from the front, the curve of Wilson contacts the buccal and lingual cusps of the molars and is lower in the middle due to the lingual inclination of the long axes of the mandibular molars. This disclosure contemplates that the curve of Wilson can be obtained from the maxillary and mandibular dental models. For example, the curve of Wilson for the maxillary model can be formed by the buccal and palatal cusps of the molars. And, the curve of Wilson for the mandibular model can be formed by the buccal and lingual cusps of the molars. The shape and the curves of Wilson for the maxillary and mandibular models should be close. Alternatively or additionally, the smoothness of the upper dental arch curvature can be used as a constraint.

Figure 5:
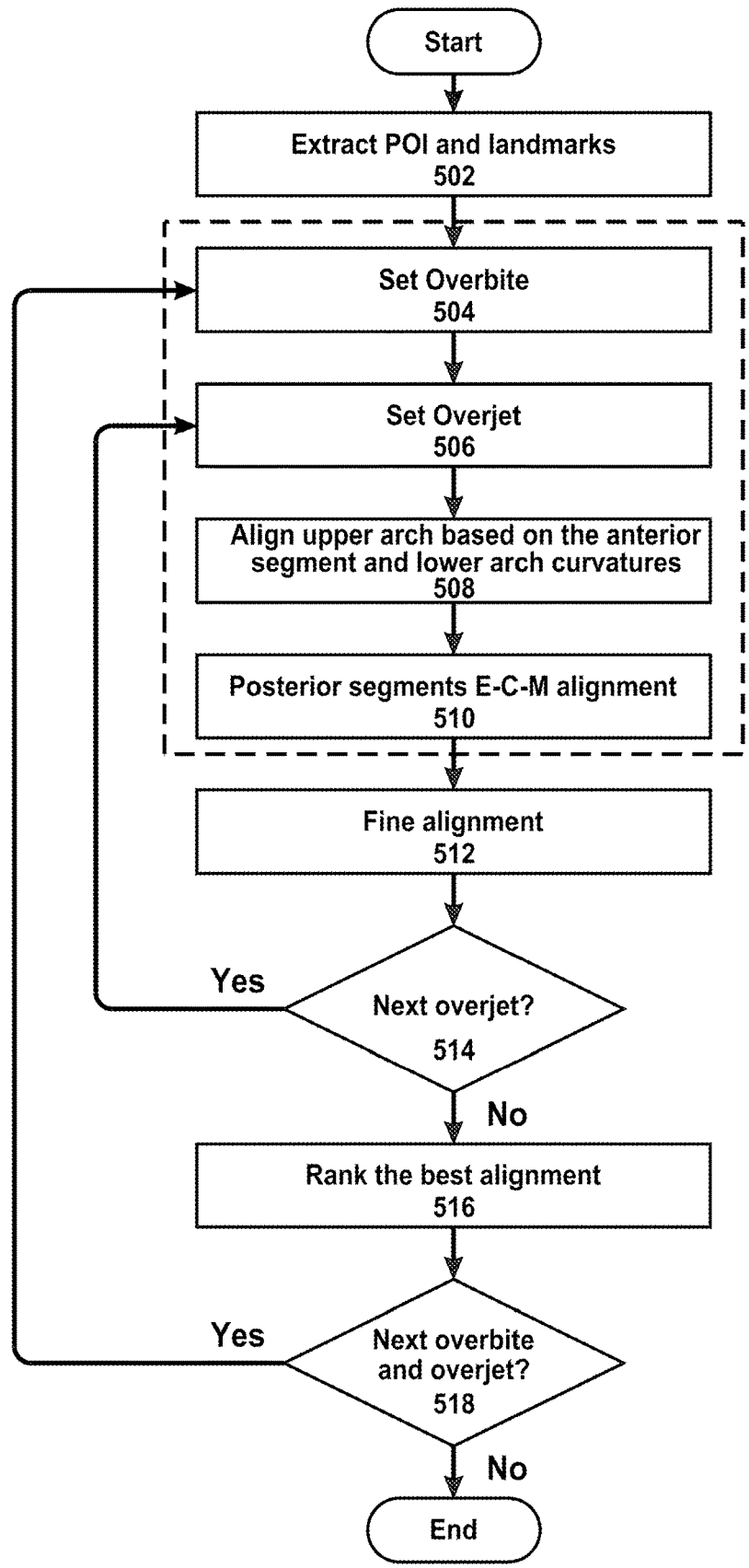
FIG. 5 is a flowchart illustrating example operations for establishing dental occlusion for 3-piece maxillary orthognathic surgeries according to an implementation described herein.
Figure 6A:
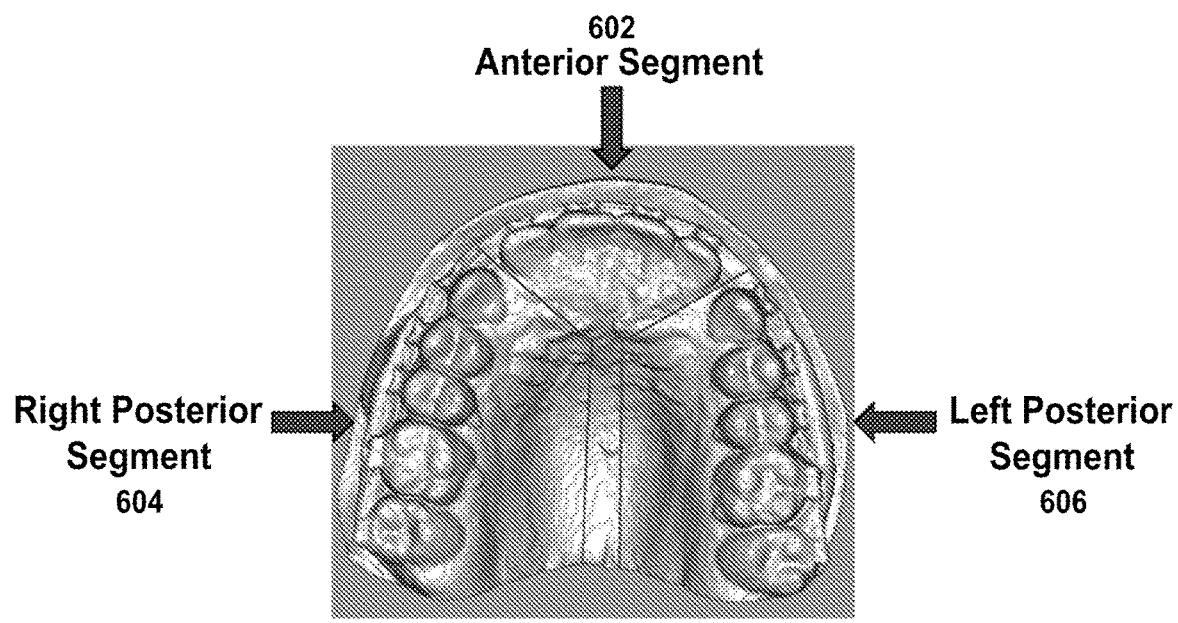
FIGS. 6A-6B illustrate example maxillary and mandibular models for 3-piece maxillary orthognathic surgeries according to an implementation described herein.
Figure 6B:
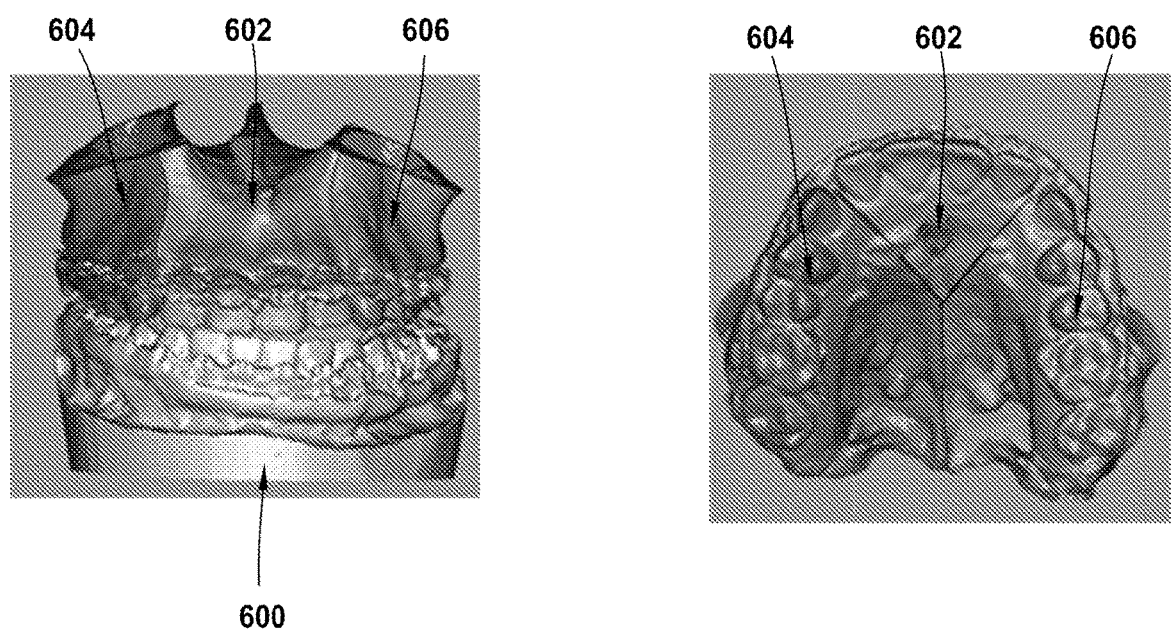

Referring now to FIG. 5, an example method for establishing dental occlusion for 3-piece maxillary orthognathic surgeries is described. This disclosure contemplates that the operations described herein can be implemented by a computing device (e.g., computing device 800 shown in FIG. 8). As described above, the method for establishing dental occlusion operates on 3D models generated from 3D images acquired by a scanner, e.g., CBCT or 3D surface/intraoral scanner. As shown in FIGS. 6A-6B, the maxillary dental model includes three pieces or segments. FIGS. 6A-6B illustrate the anterior segment 602, the right posterior segment 604, and the left posterior segment 606 of the maxillary dental model. In this case, the maxillary dental models includes three segments. Additionally, as shown in FIG. 6B, the segments of the maxillary dental model are articulated relative to a mandibular dental model 600. For 3-piece surgeries, the lower teeth model (or "mandibular model") remains static, while each piece of the upper dental model (or "maxillary dental model") is translationally and rotationally transformed and articulated to the lower teeth model.

Referring again to FIG. 5, a POI and a plurality of dental landmarks are extracted from each of the maxillary and mandibular dental models (see e.g., models shown in FIGS. 6A-6B) at step 502. POI and dental landmark extraction is described above with regard to step 102 of FIG. 1 and is therefore not described in further detail below.

At step 504, the overbite is set. Overbite can be set by the surgeon. The overbite range is customizable. For example, overbite may be in a range from 1.5 to 4 millimeters (mm), every 0.5 mm increment. It should be understood that the range and/or increment above are provided only as examples and can have other values.

At step 506, the overjet is set. Overjet can be set by the surgeon. The overjet range is customizable. For example, overjet may be in a range from 1.5 to 4 mm, every 0.5 mm increment. It should be understood that the range and/or increment above are provided only as examples and can have other values. It should also be understood that the interincisal angle changes automatically based on the given overbite and overjet.

For the given overbite and overjet (e.g., set at steps 504 and 506), the maxillary model is articulated relative to the mandibular model according to the respective dental midlines and arch curvatures of the anterior segment and lower dental arch at step 508. Additionally, at step 510, each of the right and left posterior segments of the maxillary model is separately articulated according to the E-C-M relationship. The E-C-M relationship considers the gap and resulted step between lateral incisor and canine (where the embrasure is originally located), and Class I canine and Class I molar relationship. It should be understood that the steps of FIG. 5 shown in the dotted box achieve the alignment accomplished by step 106A of FIG. 1 for 1-piece maxillary orthognathic surgeries.

At step 512, the alignment of the maxillary and mandibular models is fine tuned. For example, each of the anterior, right posterior, and left posterior segments of the maxillary model are adjusted to achieve the maximum contact with the collision constraint. This ensures that the maxillary and mandibular models do not penetrate one another as a result of the alignment performed at step 508 and 510. The previously established arch curvature relationship (step 508) and/or E-C-M relationship (step 510) is maintained during the fine alignment of step 512.

Optionally, as described above for 2-piece surgeries, the alignment of the maxillary and mandibular models can be constrained by the distance between the individual segments (e.g., anterior/right posterior or anterior/left posterior). The individual segments should not get too close (i.e., to avoid collisions between the bones). Additionally, the gap between the individual segments (e.g., anterior/right posterior or anterior/left posterior) should be less than the limit of mucosa stretch, which is about 5 mm. Such constraint can be accomplished by limiting the distance between the cutting surfaces of the individual segments. Alternatively or additionally, the smoothness of the upper dental arch curvature can be used as a constraint. The shape and the curve of Wilson of upper dental arch should also be close to the shape and the curve of Wilson of the lower dental arch.

At step 514, steps 506 through 512 can be repeated iteratively for multiple overjet values. Optionally, at step 516, the maxillary models with different overbite values are ranked to find the best case. Optionally, at step 518, steps 504 through 516 can be repeated iteratively for multiple overbite and overjet value combinations.

Figure 7:
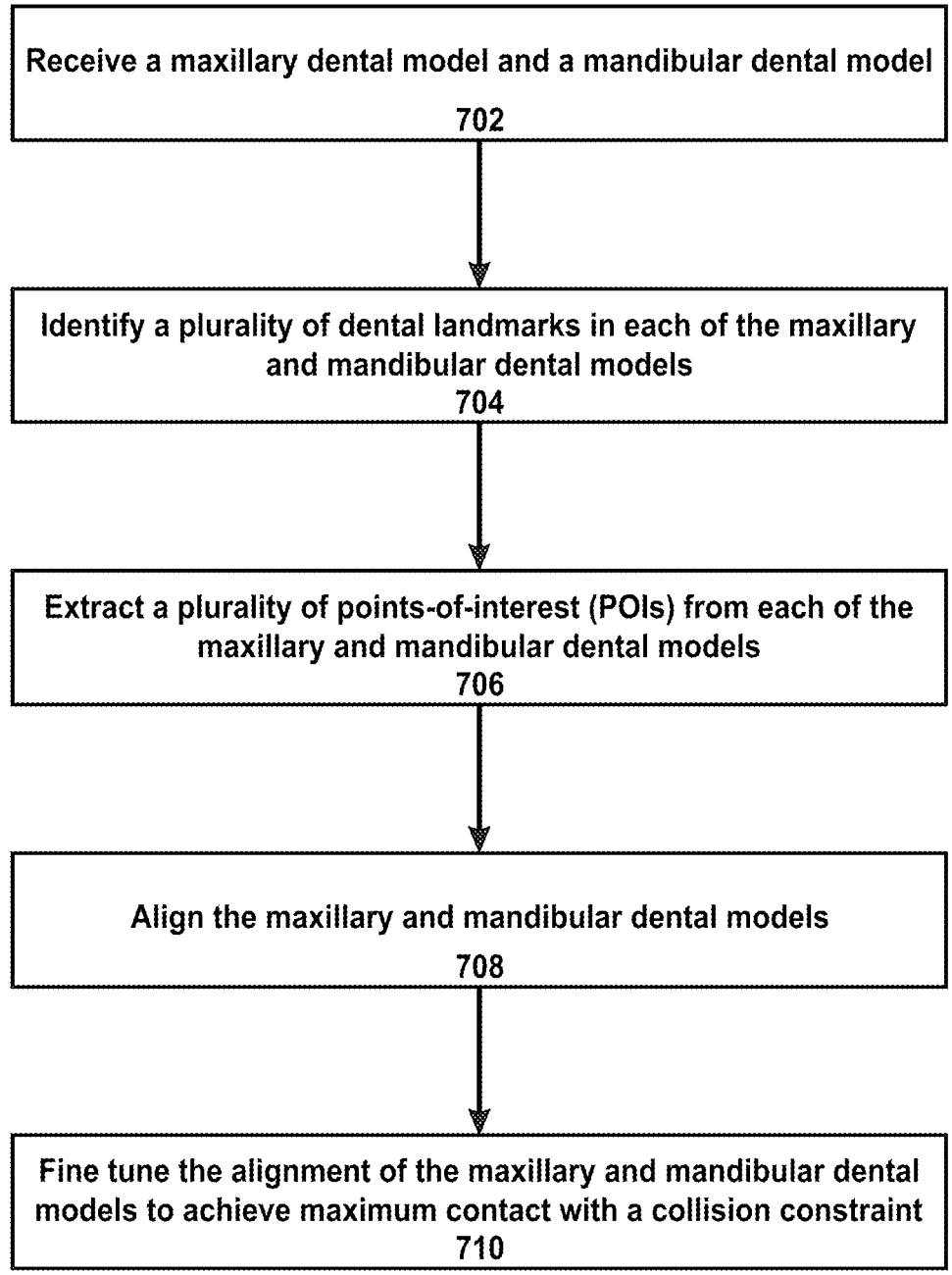
FIG. 7 is a flowchart illustrating example operations for establishing dental occlusion for orthognathic surgeries according to an implementation described herein.

Referring now to FIG. 7, an example computer-implemented method for establishing dental occlusion is described. This disclosure contemplates that the operations described herein can be implemented by a computing device (e.g., computing device 800 shown in FIG. 8). At step 702, a maxillary dental model and a mandibular dental model is received, for example, at the computing device. As described above, the maxillary and mandibular dental models may be 3D models generated from 3D images such as those captured by CBCT, 3D surface scanner, or intraoral scanner.

At step 704, a plurality of dental landmarks in each of the maxillary and mandibular dental models are identified. The dental landmarks include a plurality of maxillary dental landmarks and a plurality of mandibular dental landmarks. For example, the dental landmarks include at least one of a midpoint between central incisors, a cusp point, a groove point, or an embrasure between teeth. Dental landmarks can include the dental landmarks listed in Tables 1 and 2. It should be understood that the dental landmarks described herein are provided only as examples and that other dental landmarks can be identified and used in the methods described herein. In some implementations, the dental landmarks are identified by a user such as a surgeon (see Table 1). Alternatively or additionally, in other implementations, the dental landmarks are detected automatically (see Table 2). This disclosure contemplates using any known techniques for automatically detecting dental landmarks including, but not limited, to techniques based on machine learning.

At step 706, a plurality of points-of-interest (POI) are extracted from each of the maxillary and mandibular dental models. For example, the points-of-interest extracted from each of the maxillary and mandibular dental models are on respective occlusal surfaces of the maxillary and mandibular dental models. The POI are therefore extracted from the maxillary and mandibular occlusal surface models. Extracting POI from the occlusal surface models takes less time and is more computationally efficient than extracting POI directly from the maxillary and mandibular dental models themselves.

As described in detail herein, POI extraction can be accomplished by extracting respective occlusal surfaces of the maxillary and mandibular dental models (e.g., occlusal surface models), extracting the points-of-interest from the respective maxillary and mandibular occlusal surface models, and classifying a plurality of convex and concave points from among the points-of-interest. A POI extraction technique is described in detail below in Example 1. The convex and concave points represent the cusps and grooves of the teeth. Accordingly, a plurality of cusps on the occlusal surfaces of the maxillary dental model can be identified using the convex points, and a central groove in the occlusal surfaces of the mandibular dental model can be identified using the concave points. In this case, the cusps of the maxillary teeth correspond to the central groove of the mandibular teeth. Alternatively or additionally, a plurality of cusps on the occlusal surfaces of the mandibular dental model can be identified using the convex points, and a central groove in the occlusal surfaces of the maxillary dental model can be identified using the concave points. In this case, the cusps of the mandibular teeth correspond to the central groove of the maxillary teeth.

At step 708, the maxillary and mandibular dental models are aligned. As described above, for 1-piece surgeries, the mandibular dental model remains static, while the maxillary dental model is translationally and rotationally transformed and articulated to the mandibular dental model in some implementations, while in other implementations the maxillary dental model may remain static, while the mandibular dental model is translationally and rotationally transformed and articulated to the maxillary dental model. For 2- and 3-piece surgeries, the mandibular dental model remains static, while individual segments of the maxillary dental model are translationally and rotationally transformed and articulated to the mandibular dental model. Additionally, as described herein, for 1-piece orthognathic surgeries, the maxillary and mandibular dental models are aligned according to the relationship between dental landmarks (e.g., M-C-M relationship) or according to the respective curvatures of the upper and lower teeth. In the former case (dental landmark relationships), the step of aligning the maxillary and mandibular dental models includes aligning a midline pair of maxillary and mandibular dental landmarks mediolaterally and minimizing a sum of distances between at least one pair of the maxillary and mandibular dental landmarks. The midline pair is a pair of the midpoint between the right and left maxillary central incisors and the midpoint between the right and left mandibular central incisors. Additionally, the at least one pair of the maxillary and mandibular dental landmarks includes at least one canine or embrasure pair of the maxillary and mandibular dental landmarks and at least one molar pair of the maxillary and mandibular dental landmarks. Thus, for M-C-M alignment, the midline pair and at least one of the canine-embrasure pairs are aligned along the tangent line of the dental arch, and the molar pair is aligned (minimize distance) in three dimensions (mediolaterally, superoinferiorly, and anteroposteriorly). In the latter case (arch curvatures), the step of aligning the maxillary and mandibular dental models includes aligning an upper dental curve to a lower dental curve. The dental curves of the upper and lower dental arches are obtained by fitting a curve to the respective dental landmarks of the maxillary and mandibular dental models. As described above, an optimal reference frame for each curve can then be estimated, e.g., using PAMED method. Finally, after registering the midpoints between the right and left central incisor of the upper and lower dental curves, U0 and L0, the reference frames of the maxillary and mandibular dental models are aligned together.

At step 710, the alignment of the maxillary and mandibular dental models is fine tuned to achieve maximum contact with a collision constraint. This guarantees that the maxillary and mandibular occlusal models do not penetrate one another as a result of the alignment performed at step 708. A technique for collision constraint is described in detail in Example 1 below. In some implementations, the aligned maxillary and mandibular dental models represent a dental occlusion. Alternatively or additionally, in some implementations, the aligned maxillary and mandibular dental models represent an optimal position for a next stage of orthodontic treatment.

For 2-piece orthognathic surgeries, the maxillary dental model includes a plurality of individual segments, for example, a major segment and a minor segment in some implementations. In this implementation, the step of aligning the maxillary and mandibular dental models (e.g., step 708) includes aligning the major segment of the maxillary dental model and the mandibular dental model according to the M-C-M relationship, and thereafter aligning the minor segment of the maxillary dental model and the mandibular dental model according to the E-C-M relationship. The major segment M-C-M alignment may include aligning a midline pair and at least a canine or embrasure pair of the maxillary and mandibular dental landmarks along the tangent line of the dental arch, and minimizing a sum of distances between at least one molar pair of the maxillary and mandibular dental landmarks. The minor segment E-C-M alignment may include minimizing a sum of distances between an embrasure between teeth of the major and minor segments of the maxillary dental model, at least one canine, premolar or embrasure pair of the maxillary and mandibular dental landmarks, and at least one molar pair of the maxillary and mandibular dental landmarks. Alternatively or additionally, the minor segment E-C-M alignment may include aligning the minor segment of the maxillary dental model and the mandibular dental model by aligning an embrasure between teeth of the major and minor segments of the maxillary dental model and at least one canine, premolar or embrasure pair of the maxillary and mandibular dental landmarks along the tangent line of the dental arch, and by minimizing a sum of distances between at least one molar pair of the maxillary and mandibular dental landmarks.

In other implementations of 2-piece orthognathic surgeries, the maxillary dental model includes a plurality of individual segments, for example, a right segment and a left segment. In this implementation, the step of aligning the maxillary and mandibular dental models (e.g., step 708) includes separately aligning each of the right and left segments of the maxillary dental model and the mandibular dental model according to the M-C-M relationship. The M-C-M alignment may include aligning a midline pair and at least a canine or embrasure pair of maxillary and mandibular dental landmarks along the tangent line of the dental arch, and minimizing a sum of distances between at least one molar pair of the maxillary and mandibular dental landmarks.

Optionally, for 2-piece orthognathic surgeries, the alignment of the maxillary and mandibular dental models can be constrained by the distance between the individual segments (e.g., major/minor or right/left). The individual segments should not get too close (i.e., to avoid collisions between the bones). Additionally, the gap between the individual segments (e.g., major/minor or right/left) should be less than the limit of mucosa stretch, which is about 5 mm. In other words, the maxillary segments should not be separated by a distance exceeding anatomical limit. In addition, the respective curves of Wilson of the aligned maxillary and mandibular models should be close to each other. This allows the surgeons to consider clinical criteria.

For 3-piece orthognathic surgeries, the maxillary dental model includes a plurality of individual segments, for example, an anterior segment and left and right posterior segments. In this implementation, an overbite and overjet are received, for example at the computing device. Additionally, the step of aligning the maxillary and mandibular dental models (e.g., step 708) includes aligning the maxillary and mandibular models mediolaterally by the midline pair of the maxillary and mandibular dental landmarks mediolaterally; and superoinferiorly and anteroposteriorly by considering appropriate overjet, overbite or other clinical parameter specified by user. This aligns the mediolateral, superoinferior, and anteroposterior translations. In addition, the step of aligning the maxillary and mandibular models (e.g., step 708) includes aligning the maxillary and mandibular models by considering a curvature of the anterior segment of the maxillary dental model to a curvature of the mandibular dental model. This aligns the pitch, roll, and yaw rotations. Accordingly, the alignment is in six degrees-of-freedom. Thereafter, each of the left and right posterior segments of the maxillary dental model and the mandibular dental model are aligned according to the E-C-M relationship. This is accomplished by minimizing a sum of distances between an embrasure between teeth of the anterior and posterior segments of the maxillary dental model, at least one canine, premolar, or embrasure pair of the maxillary and mandibular dental landmarks, and at least one molar pair of the maxillary and mandibular dental landmarks. Alternatively or additionally, the left and right posterior segments E-C-M alignment may include aligning each of left and right posterior segments of the maxillary dental model and the mandibular dental model by aligning an embrasure between teeth of the anterior and posterior segments of the maxillary dental model and at least one canine, premolar or embrasure pair of the maxillary and mandibular dental landmarks along the tangent line of the dental arch, and by minimizing a sum of distances between at least one molar pair of the maxillary and mandibular dental landmarks. Optionally, the maxillary and mandibular dental models are iteratively aligned for each of a plurality of overbites and/or overjets. Additionally, the iteratively aligned maxillary and mandibular dental models are optimally ranked to determine a best fit.

Optionally, for 3-piece orthognathic surgeries, the alignment of the maxillary and mandibular dental models can be constrained by the distance between the individual segments (e.g., anterior/right posterior, anterior/left posterior or right posterior/left posterior). The individual segments should not get too close (i.e., to avoid collisions between the bones). Additionally, the gap between the individual segments (e.g., anterior/right posterior, anterior/left posterior or right posterior/left posterior) should be less than the limit of mucosa stretch, which is about 5 mm. In other words, the maxillary and mandibular dental models should not be separated by a distance exceeding anatomical limit. In addition, the respective curves of Wilson of the aligned maxillary and mandibular dental models should be close to each other. This allows the surgeons to consider clinical criteria.

It should be appreciated that the logical operations described herein with respect to the various figures may be implemented (1) as a sequence of computer implemented acts or program modules (i.e., software) running on a computing device (e.g., the computing device described in FIG. 8), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 8:
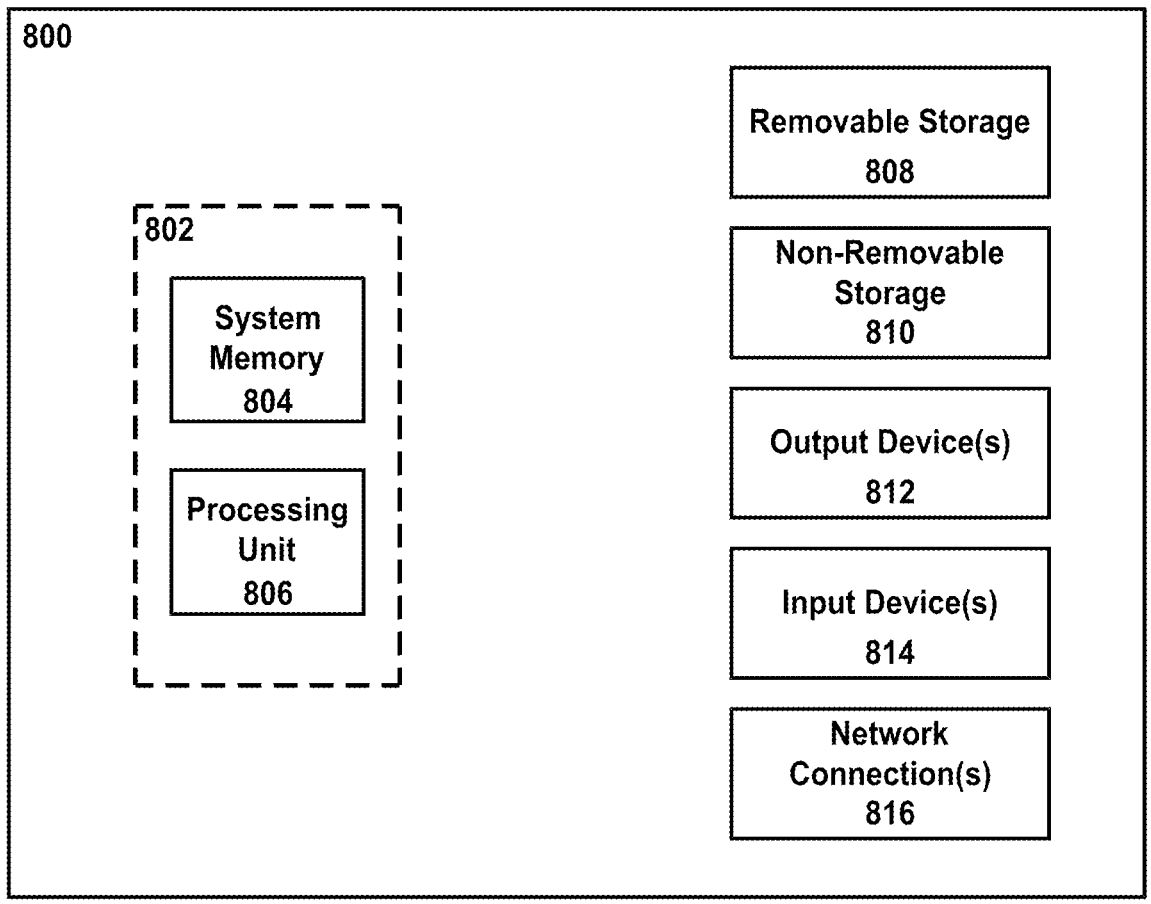
FIG. 8 is an example computing device.

Referring to FIG. 8, an example computing device 800 upon which the methods described herein may be implemented is illustrated. It should be understood that the example computing device 800 is only one example of a suitable computing environment upon which the methods described herein may be implemented. Optionally, the computing device 800 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 800 typically includes at least one processing unit 806 and system memory 804. Depending on the exact configuration and type of computing device, system memory 804 may be volatile (such as random access memory (RAM)), non-volatile (such as read-only memory (ROM), flash memory, etc.), or some combination of the two. This most basic configuration is illustrated in FIG. 8 by dashed line 802. The processing unit 806 may be a standard programmable processor that performs arithmetic and logic operations necessary for operation of the computing device 800. The computing device 800 may also include a bus or other communication mechanism for communicating information among various components of the computing device 800.

Computing device 800 may have additional features/functionality. For example, computing device 800 may include additional storage such as removable storage 808 and non-removable storage 810 including, but not limited to, magnetic or optical disks or tapes. Computing device 800 may also contain network connection(s) 816 that allow the device to communicate with other devices. Computing device 800 may also have input device(s) 814 such as a keyboard, mouse, touch screen, etc. Output device(s) 812 such as a display, speakers, printer, etc. may also be included. The additional devices may be connected to the bus in order to facilitate communication of data among the components of the computing device 800. All these devices are well known in the art and need not be discussed at length here.

The processing unit 806 may be configured to execute program code encoded in tangible, computer-readable media. Tangible, computer-readable media refers to any media that is capable of providing data that causes the computing device 800 (i.e., a machine) to operate in a particular fashion. Various computer-readable media may be utilized to provide instructions to the processing unit 806 for execution. Example tangible, computer-readable media may include, but is not limited to, volatile media, non-volatile media, removable media and non-removable media implemented in any method or technology for storage of information such as computer readable instructions, data structures, program modules or other data. System memory 804, removable storage 808, and non-removable storage 810 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 806 may execute program code stored in the system memory 804. For example, the bus may carry data to the system memory 804, from which the processing unit 806 receives and executes instructions. The data received by the system memory 804 may optionally be stored on the removable storage 808 or the non-removable storage 810 before or after execution by the processing unit 806.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, etc.), but some errors and deviations should be accounted for.

Example 1

An important step in routine orthognathic surgery is to reestablish a desired final dental occlusion. Traditionally, the final occlusion is established by hand articulating stone dental models. To date, there are still no effective solutions to establish the final occlusion in computer-aided surgical simulation. In this study, the most common one-piece maxillary orthognathic surgery is considered and a three-stage approach to digitally and automatically establish the desired final dental occlusion is described.

The technique includes three stages: (1) extraction of points of interest and teeth landmarks from a pair of upper and lower dental models; (2) establishment of Midline- Canine-Molar (M-C-M) relationship following the clinical criteria on these three regions; and (3) fine alignment of upper and lower teeth with maximum contacts without breaking the established M-C-M relationship.

As described below, this technique has been quantitatively and qualitatively validated using 18 pairs of dental models. Qualitatively, experienced orthodontists assess the algorithm-articulated and hand-articulated occlusions while being blind to the methods used. They agreed that occlusion results of the two methods are equally good. Quantitatively, the distances between selected landmarks on upper and lower teeth were measured and compared for both algorithm-articulated and hand-articulated occlusions. The results showed that there was no statistically significant difference between the algorithm-articulated and hand-articulated occlusions. The proposed three-stage automatic dental articulation method is therefore able to articulate the digital dental model to the clinically desired final occlusion accurately and efficiently. This allows doctors to completely eliminate the use of stone dental models during orthognathic surgical planning.

INTRODUCTION

In the last decade, computer-aided surgical simulation (CASS) [1, 2] has become a standard of care for orthognathic surgical planning. Orthognathic surgery is specifically designed to correct jaw deformities, and due to the complex nature of the human face, orthognathic surgery requires extensive surgical planning. Using CASS, surgeons are able to plan the entire surgery on the computer.

An important procedure in surgical planning is to establish a desired "final dental occlusion." The current clinical process is to manually articulate the upper and lower stone dental models together by following the clinical guidelines, i.e., midline alignment, Class I canine relationship, Class I molar relationship, and maximum upper and lower teeth contact (see FIGS. 9A-9C), as well as utilizing the instant tactile response to articulate the teeth models. However, unlike in the physical world, the digital teeth models are composed of point clouds which can penetrate into each other regardless of collision between them. For this reason, current CASS planning still requires the traditional dental articulation, in which surgeons are forced to pour the stone models from the dental impression or print the intraorally scanned teeth three-dimensionally, hand-articulate them to the desired final occlusion, and then scan the occluded models together. This is an unnecessary and redundant task, especially when surgeons and orthodontists use an intraoral scanner, which has gained more popularity nowadays and is becoming a standard acquisition tool for dental models.

There are only a few reports on digitally establishing dental occlusion [3-6]. However, these conventional methods either require extensive pre-processing or use a haptic feedback device to guide the articulation. Thus, none of these conventional methods have been successfully utilized in clinical practice.

A three-stage approach to automatically articulate the dental models to clinical desired final occlusion for routine orthognathic surgery, in which presurgical orthodontic treatment should be completed, is described below. The proposed technique includes the following: (1) it utilizes clinical criteria to establish the best possible final dental occlusion as done by surgeons clinically; (2) it is fully automatic and completely eliminates the need for human intervention to generate the digital dental models; and (3) it is computationally efficient. In clinic practice, this approach will ultimately eliminate the need of stone dental models and hand articulation and thus significantly simplify the surgical planning process.

Method

Ideally in clinical practice, the upper and lower teeth should be occluded as follows. In the incisal region, the upper and lower dental midlines should be perfectly aligned with each other (called midline alignment, FIG. 9A), while each lower incisal edge should make maximum contact to the palatal surface of the corresponding upper incisors. In the canine region, the upper canine should be visually aligned to the buccal side of the embrasure between the corresponding lower canine and first premolar (called Class I canine relationship, FIG. 9B). In the molar region, the mesiobuccal cusp of the upper first molars should be visually aligned to (the buccal side of) the developmental groove of the lower first molar (called Class I molar relationship, FIG. 9B).

Figures 9A, 9B, 9C:
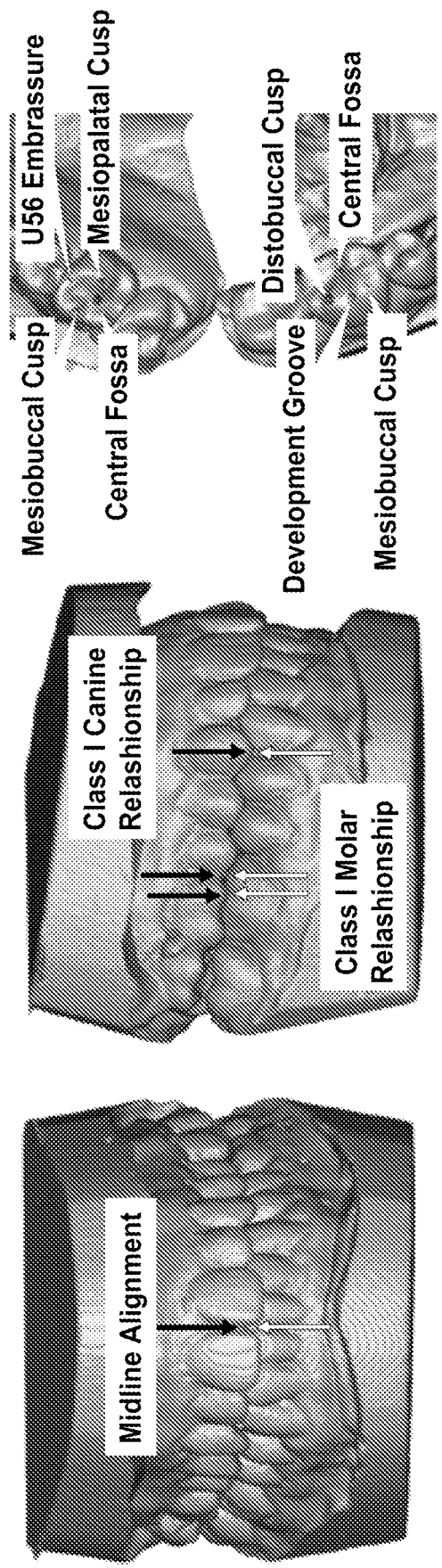
FIGS. 9A-9C illustrate the occlusion relationship.

The automatic dental articulation approach described herein is to digitally "replicate" the above steps that doctors do clinically. In addition, the molar relationship is determined by a true quantitative cusp-fossa relationship, rather than a qualitative visual alignment. That is, the mesiopalatal cusp of the upper first molar is seated in the central fossa of the corresponding lower first molar with maximum contact. Also, the distobuccal cusp of the lower first molar is seated in the central fossa of the corresponding upper first molar, also with maximum contact (FIG. 9C).

Figure 10:
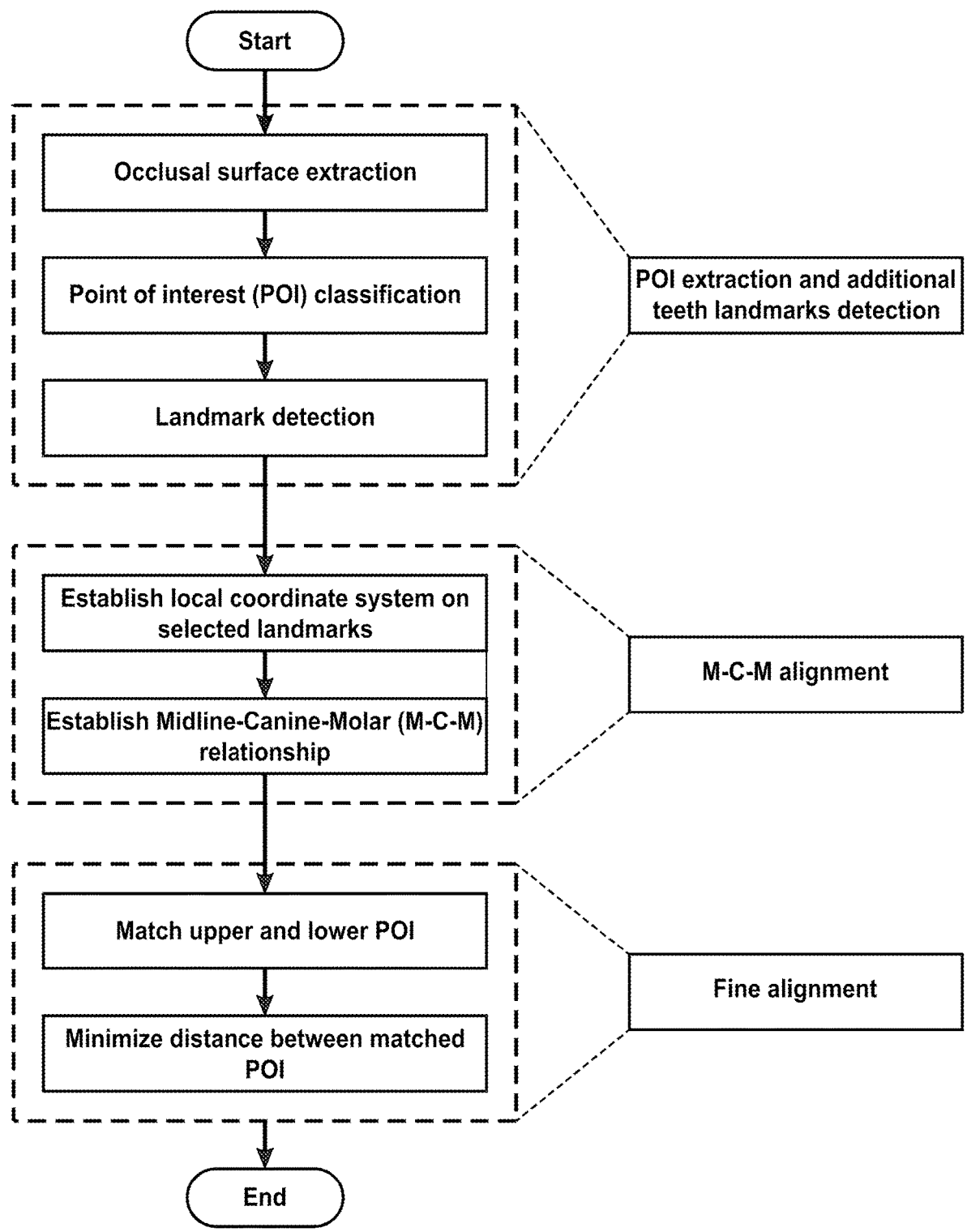
FIG. 10 is a flowchart of an algorithm-articulation method according to an implementation described herein.

This approach includes the following three stages: (1) extract points of interest (POI) and detect additional teeth landmarks; (2) establish clinically desired Midline-Canine-Molar (M-C-M) relationship, and (3) establish final occlusion to achieve maximum contact between upper and lower dental models with collision and clinical (the desired M-C-M relationship) constraints. During the second and third stages, the upper dental model is mobile while the lower dental model remains static. The flowchart is shown in FIG. 10. Details of each stage are described below.

Extract Points-of-Interest and Detect Additional Teeth Landmarks

Each dental model is a triangulated mesh in STL format containing the teeth, braces, and gingiva parts. However, only the anatomical structures on the occlusal surface, including peaks (e.g., incisal edges and cusps) and valleys (e.g., fossae, embrasures and central grooves), are involved in the dental articulation. Therefore, POI are extracted to represent these anatomical structures which are clinically important in guiding the digital articulation. While most teeth landmarks (with known anatomical definitions and names) are already digitized by surgeons during the surgical planning process (see FIG. 11, Table 1), it is necessary to detect the teeth landmarks that are not commonly used for surgical planning but important for articulation (see FIG. 12, Table 2). The POI extraction and the teeth landmark detection are automatically achieved in the following four steps.

Extraction of Occlusal Surfaces

Figure 13B:
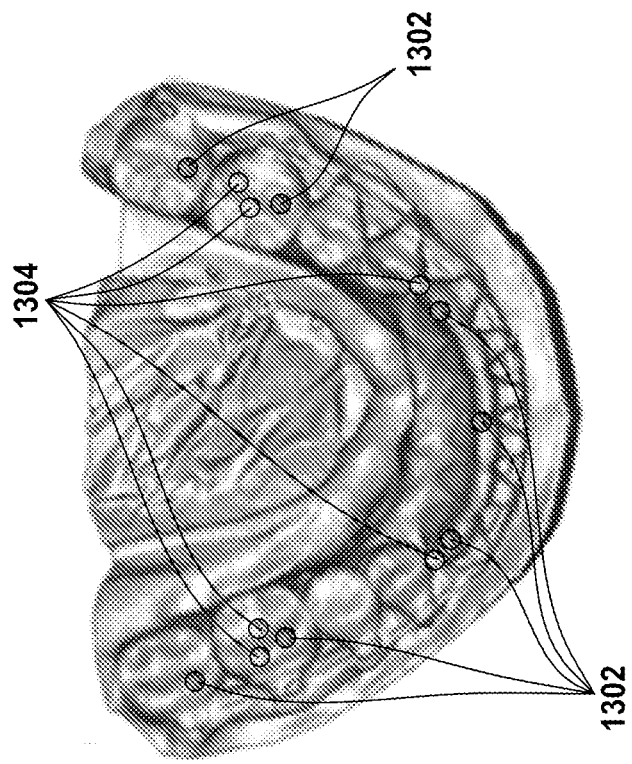
FIGS. 13A-13B illustrate landmarks for digital occlusion (red 1302: digitized landmarks; green 1304: detected landmarks).
Figure 13A:
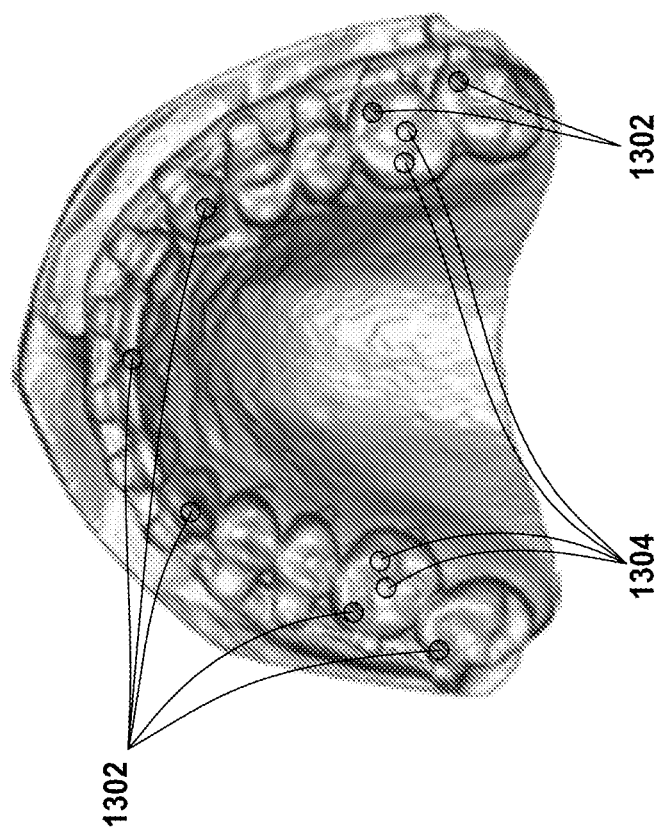

The patient's dental models usually include braces, gums and base, which cause severe interference for the digital articulation. This step is to extract the occlusal surface by digitally removing the braces and gums with the guidance of the already digitized teeth landmarks. The digitized landmarks are shown in FIGS. 13A-13B and listed in Table 1.

Figure 14A:
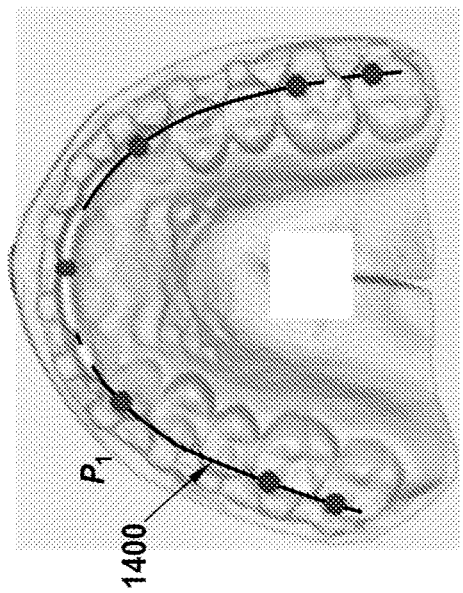
FIGS. 14A-14C illustrate occlusal surface extraction.
Figure 14B:
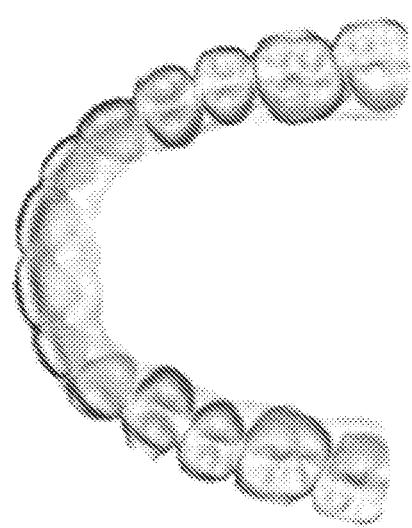
Figure 14C:
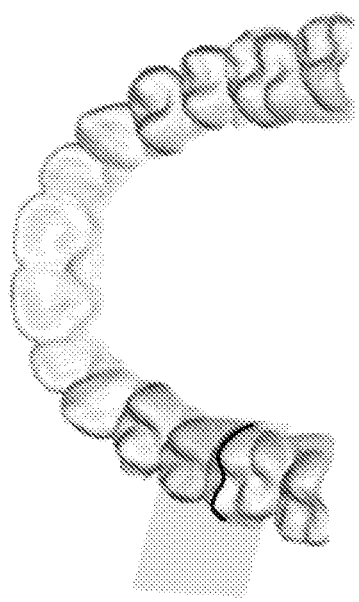

For each dental model, seven already digitized teeth landmarks (Table 1) are first used to create a 200-point fitting curve $Cur'_1$ (element 1400 in FIG. 14A) and a plane P1 by principle component analysis (PCA). Then $Cur'_1$ is projected onto P1, denoted by $Cur'_1$. Each vertex v (point) of the dental model is also projected to $P_1$, denoted by v'. The distance $h_v$ between v and v' is calculated for each vertex. After that, the distance $r_v$ between each projected vertex v' and the projected fitting curve $Cur'_1$ is calculated. The vertices of the occlusal surface are ultimately extracted using k-means clustering method. A threshold H is set empirically for $h_v$. For each vertex u satisfying $h_u < H$, a parameter $\phi_u$: $=\alpha \cdot h_u + \beta \cdot r_u$ is defined, where coefficients $\alpha$ and $\beta$ satisfy $\alpha + = 1$. The values were empirically chosen as H=15 mm, $\alpha$=0.2. The values of $\alpha$ and $\beta$ control the importance of $h_u$ and $r_u$ in parameter $\phi_u$. In the next step, k-means clustering algorithm is performed using parameter $\phi_u$. Among the acquired clusters, the cluster for the occlusal surface only is kept (FIG. 14B). Finally, 200 cross-sectional planes are created, one for each point on $Cur'_1$. The intersection of the plane and occlusal surface and subsequently its envelope Env are calculated. FIG. 14C shows one envelope as an example. The envelopes are used to further classify the peaks and valleys on the occlusal surface.

POI Classification

Each envelope consists of three POI: one valley in the middle and two peaks, one on each side (buccal and palatal/lingual). The points of the prominent peak on one side are first detected, then the second peak on the other side is detected, and finally the points of the valley are detected.

Figure 15A:
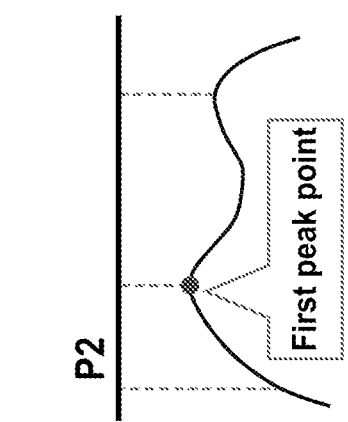
FIGS. 15A-15D illustrate POI classification.

Detect the points of the first (the prominent) peak. A plane $P_2$ is created. It is parallel to $P_1$ with a distance in the direction away from the occlusal surface (FIG. 15A). 15 mm is empirically used as this distance to ensure that $P_2$ does not touch the occlusal surface. The vertices on each envelope are then classified by calculating the distance between each vertex to $P_2$. If the distance is greater than the both of its two neighbors, this vertex is classified as the local minimum point; if the distance is smaller than its neighbors, it is classified as the local maximum point. The local maximum point with the smallest distance to $P_2$ is the most prominent peak point on each envelope ("first peak point" in FIG. 15A).

Detect the points of the second peak. The detection of the points of the second peak is more complex. Due to the teeth anatomy, the point with the second smallest distance is not the second peak's point. The following strategy is used to detect the second peak's points.

Figure 15B:
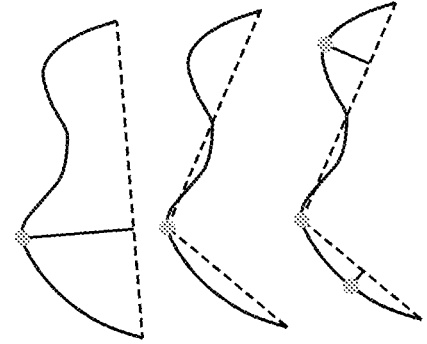

First, the envelopes of seven teeth landmarks are simplified using Douglas-Peucker algorithm (FIG. 15B). To begin, the first and last vertices of the envelope are marked as initial neighboring "keep" points. Next, each pair of two neighboring "keep" points are connected by a line segment. A distance is then calculated from each vertex on the envelope segment between the two neighboring "keep" points to the line segment. The vertex that has the largest distance is marked as "keep" if the distance is greater than an empirically defined threshold $\varepsilon$:=0.01 mm. Once a set of new "keep" points is found, the algorithm iteratively forms new line segments and repeats the above steps.

Figure 15C:
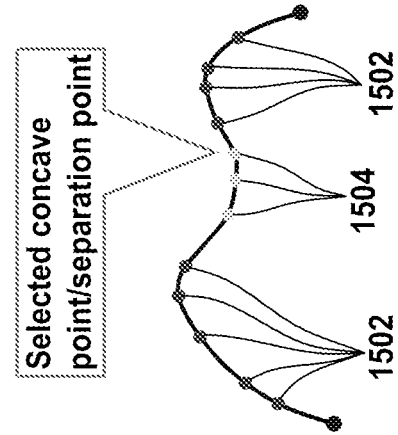

After the simplification of the seven envelopes, each "keep" point is classified as either convex (red points 1502 in FIG. 15C) if it falls on the convex part of the envelope, or concave (green points 1504 in FIG. 15C) if it falls on the concave part. A distance between each concave point and $P_2$ is calculated. Only the concave point with the largest distance is selected, one for each corresponding envelope.

A new 200-point fitting curve $Cur_2$ is created based on the seven concave points. Each point $p \in Cur_2$ is first projected onto its corresponding cross-sectional plane as p', which is then projected again to the envelope and becomes a separation point, that divides each envelope into two segments, $S_1$ and $S_2$.

Figure 15D:
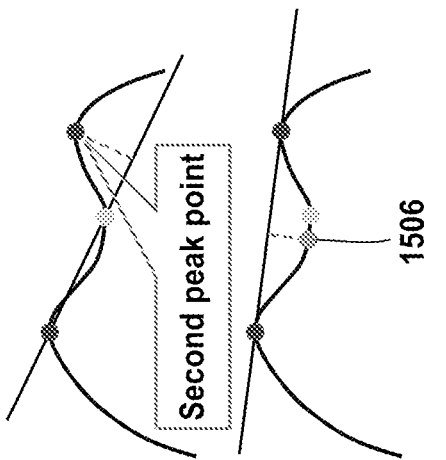

Assume the first (the prominent) peak's point falls onto one of the two envelope segments $S_1$. To detect the second peak's point on segment $S_2$, a straight line is first constructed by connecting the first peak's point and the separation point. All the local maximum points on $S_2$ that are above the straight line and in the direction away from the occlusal surface are selected. The distances between each of the selected local maximum points and the straight line are then calculated. The second peak's point is the point with the largest distance ("second peak point" on the right in FIG. 15D).

Detect the points of the valley. To detect the (deepest) valley point on each envelope, a straight line is created by connecting the two peak points. All the local minimum points below the straight line (in the direction toward the occlusal surface) and located between the two peak points are selected. The distance from each of the selected points to the straight line is calculated. The valley point is the point with the largest distance (dark green point 1506 in FIG. 15D).

Figure 16B:
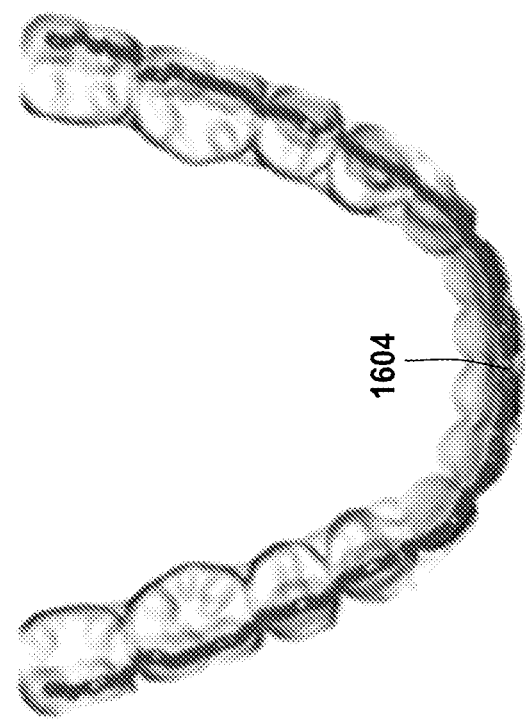
FIGS. 16A-16B illustrate extracted POI on a pair of teeth models.
Figure 16A:
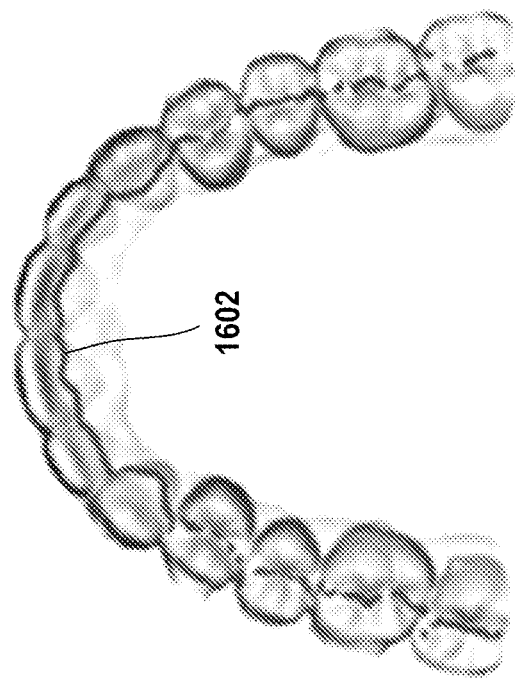

Finally, there are no valley points on the anterior teeth. Clinically, a hypothetical line that is extended from the valleys of the upper premolar and molars to the palatal surfaces of the anterior teeth is used to estimate where the lower incisal edges should occlude. In this approach, the hypothetical valley points of the anterior teeth are calculated as follows. The average distance from all premolar and molar valley points to $P_2$ is calculated. This is the same distance where the valley points are located on the palatal side of the upper incisors. The valley points of the upper model are shown in green 1602 in FIG. 16A, and the corresponding peak points of the lower model are shown in red 1604 in FIG. 16B.

Detection of Additional Landmarks

In addition to the clinically digitized teeth landmarks, five additional landmarks on each side are further needed for articulating the canine and molar relationships (green points 1304 in FIGS. 13A and 13B and also listed Table 2). They are automatically detected based on the anatomy of the teeth.

For the additional lower teeth landmarks: (1) Landmark L34Embr is the embrasure between the canine and the first premolar. It is detected as the first local minimum buccal peak point, distal to the already digitized landmarks of the canine cusp (L3C). (2) Landmark L6DBC is the distobuccal cusp of the first molar. The developmental groove is initially detected as the first local minimum buccal peak point, distal to the already digitized mesiobuccal cusp of the first molar (L6MBC). Landmark L6DBC is then detected as the first local maximum buccal peak point, distal to the developmental groove. (3) Landmark L6CF is the central fossa of the lower first molar. It is the "lowest" valley point, within the boundaries of Landmarks L6MBC mesially and L6DBC distally.

For the additional upper teeth landmarks: (1) Landmark U6MLC is the mesiopalatal cusp of the upper first molar. It is the local maximum palatal peak point, on the palatal side of the already digitized landmark of the mesiobuccal cusp of the upper first molar (U6MBC). (2) Landmark U6CF is the central fossa of the upper first molar. It is detected using the same method of detecting Landmark L6CF, by first detecting the developmental groove of the upper first molar, then the distobuccal cusp of the first molar (U6DBC). Landmark U6CF is then detected as the "lowest" valley point, within the boundaries of Landmarks U6MBC mesially and Landmark U6DBC distally.

Establish Clinically Desired Midline-Canine-Molar Relationship

In the second stage, the upper and lower dental models are aligned to the clinically desired M-C-M relationship. It is achieved in the following two steps: (1) a local coordinate system is established for each of the key landmarks on the lower dental model. These key landmarks are used for achieving M-C-M alignment; and (2) the sum of distances is minimized between the upper and lower key landmarks.

Local Coordinate System

Figures 17, 18:
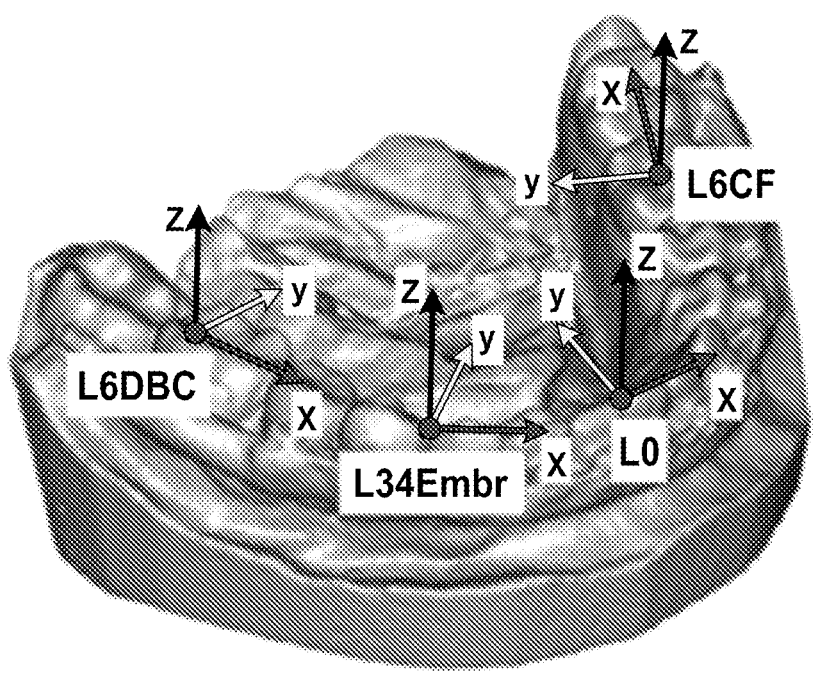
FIG. 17 is Table 3, which shows key landmarks used in M-C-M alignment.
FIG. 18 illustrates a local coordinate system for lower teeth landmarks.

During the dental alignment, the lower teeth model always remains static, while the upper dental model is translationally and rotationally transformed and articulated to the lower model. A local coordinate systems is built to establish a clinically desired M-C-M relationship on each of the 7 key landmarks of the lower teeth (FIG. 17, Table 3).

To build a local coordinate system, the same occlusal plane P1 for the lower teeth model is used. The normal vector of P1, in the direction from the root to the crown of the teeth, is the z-axis of the local coordinates for all the landmarks. The lower landmarks list in Table 3 are then projected onto P1, and a fitting curve Cur3 is formed using these projected landmarks. The tangent line of Cur3 at each projected landmark, along the direction from the (patient's) right to the left side of the dental model, is the x-axis of each corresponding landmark. Last, the y-axis is calculated as the cross product of the z- and x-axes (see FIG. 18, only one side of the landmarks are shown for bilateral landmarks).

Distance Minimization

The three clinical requirements were jointly considered as described above. Clinically, the midline alignment and the canine relationship are more important than the molar relationship because it is difficult for orthodontists to correct the midline deviation and the canine relationship after the surgery, while it is much easier to close the space between upper and lower molars. For this reason, in M-C-M alignment, different weights are assigned to the dental midline alignment, the canine relationship and the molar relationship.

$l_u$ is used to represent an upper tooth landmark and $l_l$ to represent its corresponding lower tooth landmark. The local x-axis at each lower landmark is represented by $x_l$, and the transformation matrix for upper model is M. Thus each new upper landmark position becomes $M \cdot l_u$. For the midline alignment, the deviation between U0 and L0 along the local x-axis is considered. Let $d_{mi} = M \cdot l_{U0} - l_{L0}$ be a vector pointing from L0 to U0, and $d_{mi}^x = \|d_{mi}\| \cdot x_{L0}$ be the distance of $d_{mi}$ along the local x-axis.

Similarly, for the canine relationship, we consider the off-set between the corresponding U3C and L34Embr on both right and left sides, also along their local x-axes. For each side, let $d_C = M \cdot l_{U3C} - l_{L34Embr}$ be the vectors pointing from L34Embr to U3C, and $d_C^x = \|d_C\| \cdot x_{L34Embr}$ be the distances of $d_C$ along the local x-axis.

For the molar relationship, consider the Euclidean distance between each paired upper and lower molar landmarks, i.e., the distances of U6MLC-L6CF and U6CF-L6DBC, respectively, on the right and the left sides are considered. Let $d_{M1} = M \cdot l_{U6MLC} - l_{L6CF}$ and $d_{M2} = M \cdot l_{U6CF} - l_{L6DBC}$ be the vectors pointing from the lower teeth landmarks to the corresponding upper teeth landmarks.

Three different weights, $w_1$, $w_2$ and $w_3$, are assigned to the distances of midline $d_{mi}^x$ canine $d_C^x$ and molar $\|d_{M1}\|$ and $\|d_{M2}\|$, respectively. They represent the importance ratio of the corresponding teeth taken into the M-C-M alignment. They are set to be 1 by default, indicating that midline, canine and molar are equally considered in the alignment. These weights can either be used by their default values or changed with user's preference in our user interface. The summation of the above distances is $w_1 \cdot d_{mi}^x + w_2 \cdot d_C^x + w_3 \cdot (\|d_{M1}\| + \|d_{M2}\|)$.

There are two clinical rules during the dental articulation: (1) the buccal cusps and incisal edges of the upper dental model are located at the buccal side of the lower teeth, and (2) the upper dental model is located superiorly to the lower dental model. The local y-axis and z-axis of each lower landmark are represented by $y_l$ and $z_l$. The following constraints are used to guarantee the correct position of the dental models. For the midline and the canines, the constraints are $d_{mi} \cdot y_{L0} < 0$ and $d_C \cdot y_{L34Embr} < 0$ (rule #1). For the molars the constraints are $d_{M1} \cdot z_{L6CF} > 0$ and $d_{M2} \cdot z_{L6DBC} > 0$ (rule #2).

In order to avoid collision in M-C-M relationship, the constraints for the molars are modified (relaxed) as $(M \cdot l_{U6MBC} - l_{L6MBC}) \cdot z_{L6CF} > 0$. In addition, the constraints are modified as $d_C \cdot z_{L34Embr} > 0$. This is to ensure U6MBC is above L6MBC, and U3C is above L34Embr.

Finally, the optimization function can be written as:

$$\text{Min } \{w_1 \cdot d_{mi}^x + w_2 \cdot d_C^x + w_3 \cdot (\|d_{M1}\| + \|d_{M2}\|)\} \quad (1)$$

$$\text{s.t. } d_{mi} \cdot y_{L0} < 0,$$

$$d_C \cdot y_{L34Embr} < 0,$$

$$d_C \cdot z_{L34Embr} > 0,$$

$$(M \cdot l_{U6MBC} - l_{L6MBC}) z_{L6CF} > 0$$

Points-of-Interest-Based Fine Alignment

In this stage, the upper and lower dental models are finally articulated to the clinically desired final occlusion by iteratively minimizing the distance between the upper and lower POI. This is also to achieve a best possible maximum contact between the upper and the lower teeth. During articulation, each upper teeth POI is matched with a lower teeth POI. Then the collision constraint and M-C-M constraint are calculated based on current upper teeth location. Finally, the teeth model is finely aligned by minimizing the distance between matched POI under these two constraints.

Point Match of Upper and Lower POI

The upper and lower teeth should follow a cusp-fossa intercuspation relationship. That is, the central groove (the valley points) of the upper teeth should be seated on top of the buccal cusps (the buccal peak points) of the lower teeth for the premolars and molars. The palatal side of the upper incisors and canines (the hypothetical valley points at the palatal side of the upper anterior teeth) should also have a maximum contact with the lower incisors and canines edges (the peak points of lower anterior teeth). Similar to the M-C-M stage that each upper teeth landmark is paired with a lower teeth landmark, each vertex of the upper POI (green points 1602 in FIG. 16A) is paired with a lower POI (red points 1604 in FIG. 16B). Let $\{u_i\}$ be the upper POI and $\{l_j\}$ be the lower POI. The pairing process is to find a $l_{j_i}$ for $u_i$, such that $l_{j_i} = \text{argmin}_{l_j \in \{l_j\}} \|u_i - l_j\|$.

Collision Constraint

Collision constraint is applied to guarantee that upper and lower models do not penetrate into each other. Theoretically, the penetration depth of upper and lower models should be 0 when there is no collision. However, due to the reconstruction error of triangulated.STL models, 0.1 mm of penetration depth is allowed empirically. Clinically, this small allowance does not result in collision between the upper and lower dental models.

Let $\{U_i\}$ be the vertices on the extracted upper occlusal surface and $\{L_j\}$ be the vertices on the extracted lower occlusal surface. To detect collision, each upper occlusal surface vertex $U_i$ is paired with the closest vertex $L_{j_i}$ on the extracted lower one using the same method described in the point match section above. The penetration depth is calculated as the distance that the upper vertex penetrated into the lower model, in the direction of the normal vector $n_j$ of the paired lower vertex. The penetration is formulated as:

$$(R \cdot U_i + t - L_{j_i}) \cdot n_{j_i} + \epsilon > 0$$

where R is rotational matrix and t is translational matrix, and E is the penetration depth set empirically.

Clinical M-C-M Constraint

In addition to the collision constraint, M-C-M relationship also needs to be maintained during the fine alignment. It is achieved by constraining the movement of the landmark U0 by setting user-adjustable thresholds for its moving distances along three local coordinate axis separately. By default, the movement threshold along x-axis guarantees that the alignment of the upper and lower midlines is within clinically acceptable deviation (0.5 mm, i.e., $d_{mi}^x < 0.5$). In addition, the movement threshold along y-axis is set to 1 mm toward the labial side to constrain the overjet (normal value: 1.5-4.0 mm), while the movement toward the lingual side is automatically constrained by collision. Finally, the movement threshold along z-axis is set to be 0.2 mm deviating from the lower teeth to constrain the overbite (normal value 1.5-4.0 mm), while the movement toward the lower teeth direction is also automatically constrained by collision. Within such a small amount of the movement, the midline alignment and canine and molar relationships will not be significantly changed.

Distance Minimization

The goal of this step is to find the transformation matrix for the upper dental model with the minimized overall distance between paired POI $\{u_i\}$ and $\{l_{j_i}\}$ with the collision and the M-C-M constraints. In each iteration, the model is rotated around a pivot center and then translated to minimize the overall distances between current paired $\{u_i\}$ and $\{l_{j_i}\}$. The pivot center is found based on the distances between upper and lower teeth vertices. The pivot center is calculated as:

$$\tilde{o} \leftarrow \frac{\sum_i w_i u_i}{\sum_i w_i} \quad \text{where } w_i \propto e^{-\|u_i - l_{j_i}\|} \quad (2)$$

is a weight assigned to vertex $u_i$. Then the distance is minimized by solving:

$$\text{Min } \Sigma_{i=1}^n \|R(u_i - \tilde{o}) + \tilde{o} + t - l_{j_i}\|^2 \quad (3)$$

where R is rotational matrix and t is translational matrix. After each iteration is completed, the upper vertices will be re-paired with lower vertices using point match described above, and the iteration will continue until Equation (3) converges.

Experiment and Results

Materials and Methods

Patient dental models between February 2017 and August 2018 were randomly selected from our large patient archive to evaluate the accuracy and efficiency of the technique described above qualitatively and quantitatively. The inclusion criteria were: (1) patients had undergone double-jaw orthognathic surgery, (2) maxillary surgery was a one-piece non-segmental Le Fort I osteotomy, (3) the occlusion was stable without rocking between the upper and lower dental models. Partially edentulous models were not excluded. A convenient sample size of 18 sets of dental models were finally selected and used for the evaluation. Of these 18 patients, three were edentulous cases who had upper and lower first premolars extracted on both sides.

The paired upper and lower digital dental models were generated by scanning the upper and lower dental stone models separately using a cone-beam computed tomography (CBCT) scanner (iCAT, Hatfield, Pa., United States). Once the landmarks were digitized (following the clinical routine of surgical planning), the approach was applied to automatically articulate the upper and lower models to the final occlusion. The default values for the weight w1, w2 and w3, i.e., w1=w2=w3=1. The algorithm-articulated occlusions served as the experimental group.

To generate the ground truth, the upper and lower stone models were hand-articulated by two experienced orthodontists. The hand-articulated stone models were scanned together as a whole using the same CBCT scanner, forming a final occlusal template. The separately scanned digital dental models were registered to the corresponding final occlusal template, resulting in the digital representation of the hand-articulated occlusions. This process is also the clinical routine in CASS-based surgical planning (see [1]). They served as the control group.

During the qualitative evaluation, the same two orthodontists, who were blinded from the articulation methods, compared the results of the experimental and control groups. Both were displayed in pair, side by side, on a large screen monitor. The orthodontists were able to freely rotate, show/hide and zoom in/out of the articulated digital dental models. They were also able to verify results in the computer using the corresponding stone models. A 3-scale visual analog scale (VAS, (1) the first set was better than the second set; (2) they were equal; and (3) the first set was worse) was used.

During the quantitative evaluation, the distances of the midline landmarks (U0-L0) and the canine landmarks (U3C-L34Embr) along their local x-axes were measured, and Euclidean distances of molar landmarks (U6MLC-L6CF) were averaged. In order to avoid possible human error caused by manual landmark digitization, the landmarks were only digitized on one model, either in experimental or control group. This model was then automatically registered to the other using surface-best-fit method, bringing the landmarks along with it [8, 9]. Finally, repeated measures analysis of variance (ANOVA) was performed to compare the measurements between experimental and control groups. Response variable was the distance between the paired landmarks. Within-factors were 2 methods (algorithm articulation and hand articulation) and 5 locations (midline, right and left canines, and right and left first molars). The assumption for the repeated measures ANOVA was tested and could not be rejected. If there was a statistically significant difference between the 2 methods, the within contrast would be further computed and the results would be reported separately. If there was no statistically significant difference, Bland and Altman method for accessing measurement agreement [10] would be used to report the difference between the algorithm-articulated and the hand-articulated occlusions.

Results

The three stage approach for digital dental occlusion described herein (also referred to as "algorithm-articulated") was successfully used to establish the final occlusion on all 18 pairs of the models. The maximal time spent on the entire process of running the 3-stage approach for each articulation was within 3 minutes.

Figure 19:
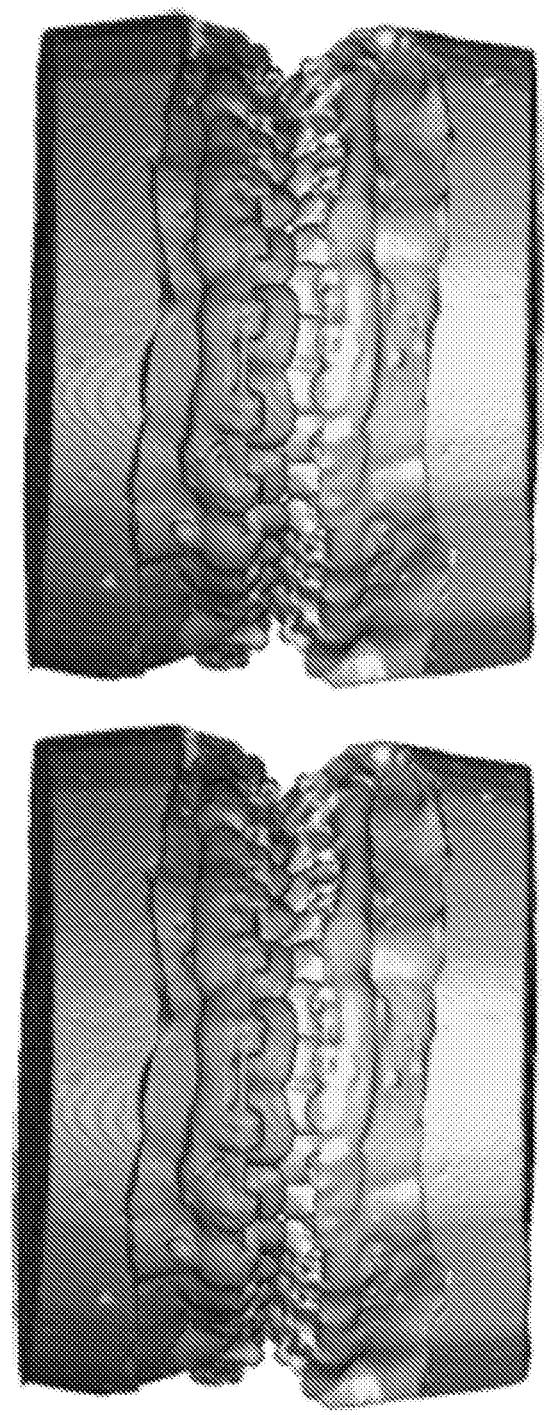
FIG. 19 illustrates an example occlusion result (left: algorithm-articulated, right: hand-articulated).

The results of the qualitative evaluation showed that all 18 algorithm-articulated models were as good as the hand-articulated ground truth models, including the edentulous cases. A randomly selected case is shown in FIG. 19.

The results of repeated measures ANOVA showed there was no statistically significant difference in the resulted occlusions between the two methods (F[1, 16]=0.02, P=0.88). Therefore, within contrast was not further computed. The mean distances are compared in FIG. 20, Table 4. The results of Bland and Altman's measurement agreement are shown in FIG. 21, Table 5. The average of the measurement differences between the two methods are less than 0.22 mm, and the lower and upper limits of the measurement differences are within the range of [−1.31, 1.25].

Discussion

The three stage approach for digital dental occlusion described herein is capable of automatically articulating the digital dental models to the clinically desired final occlusion, including several partial edentulous cases. The entire process of our method is completed within 3 minutes.

The prior knowledge is the landmarks which were clinically digitized for surgical planning. Although this study and some previous studies are able to detect landmarks by capturing certain features of the teeth, Lu et al. [11] proposed a machine learning-based method that can identify teeth as incisor, canine, premolar and molar. However, they are not able to detect the correct name for each landmark, especially for the teeth with similar teeth anatomy (e.g., first premolar and second premolar) and for those edentulous models (either with or without space between teeth).

There are studies using curvature-based methods for dental feature extraction and segmentation. Kumar et al. [12] developed mesh-based method to automatically detect cusps, ridges, grooves features. Wu et al. [4] used mean principal curvature to separate teeth for scanned dental meshes. Kumar et al. [13] used minimum principal curvature for teeth seg-mentation. Wu et al. [14] proposed a method which used mean curvature and morphologic skeleton operation to identify teeth boundaries. Mouritsen [15] proposed a method to segment teeth with an automatically adjusted curvature threshold and morphologic skeleton. However, the curvature threshold is difficult to estimate. Wang and Li [16] proposed a method based on segmentation field. However, user interaction is needed to assign boundary constraints. Surface curvature is sensitive to the anatomical structure of the teeth. However, in real life, the teeth anatomy may be different from patient to patient due to the chewing habit, teeth grinding, or developmental variations. There are also studies that developed an interactive tooth partition method based on harmonic field and prior knowledge of teeth landmarks [17, 18]. However, braces will also change the shape and features of the teeth. A projected height-based method [5] has also been developed to extract the dental feature points, in which the teeth boundary on the projection plane played an important role. However, it is also problematic when the model has braces and the structures other than the teeth, e.g., gums and the base of the dental models. These unnecessary structures significantly alter the projected teeth shape; thus, it does not work well on un-preprocessed dental models. The above methods are extremely sensitive to the orthodontic braces as they have similar geometric features as the edge and cusps. Therefore, they cannot be used on the dental models with the orthodontic braces, which nearly every patient undergoing jaw surgery would have. There are studies that integrate human interaction into the teeth segmentation [19, 20]. They have relative accurate results but need extensive human labor work.

In an effort to digitally articulate dental models, Wu et al. [4] proposed a physically based haptic simulation method to manually articulate the digital model. Nadjmi et al. [3] proposed a method using a "spring connection" to articulate the models to a stable position. It required the users to first move the upper teeth model to a good initial position and then indicate at least three pairs of points on the models for the "spring." The "spring connection" would generate force to bring upper and lower teeth together. It was not an automatic process. The articulation was highly dependent on the "lucky" initial position and the point selection. Thus, the user needed to iteratively find proper initial position in order to achieve an articulation.

In summary, the three stage approach for digital dental occlusion described herein does not require model pre-processing and the whole articulation process is fully automatic. The final occlusion result does not rely on the initial position of the teeth model, and they are evaluated to be equally good as the current gold standard. The clinical contribution of this method is significant. It allows doctors to eliminate the use of stone dental models and obtain a clinically desired final occlusion in the computer that is equally as good as the hand-articulated result.

Example 2

Methods for digital dental alignment are not readily available to automatically articulate the upper and lower jaw models. The purpose of the present study was to assess the accuracy of a 3-stage automatic digital articulation approach (see Example 1) by comparing it with the reference standard of orthodontist-articulated occlusion.

Thirty pairs of stone dental models from double-jaw orthognathic surgery patients who had undergone 1-piece Le Fort I osteotomy were used. Two experienced orthodontists manually articulated the models to their perceived final occlusion for surgery. Each pair of models was then scanned twice—while in the orthodontist-determined occlusion and again with the upper and lower models separated and positioned randomly. The separately scanned models were automatically articulated to the final occlusion using the 3-stage algorithm (see Example 1, which is also referred to below as "algorithm-articulated method"), resulting in an algorithm-articulated occlusion (experimental group). The models scanned together represented the manually articulated occlusion (control group). A qualitative evaluation was completed using a 3-point categorical scale by the same orthodontists, who were unaware of the methods used to articulate the models. A quantitative evaluation was also completed to determine whether any differences were present in the midline, canine, and molar relationships between the algorithm-determined and manually articulated occlusions using repeated measures analysis of variance (ANOVA). Finally, the mean standard deviation values were computed to determine the differences between the 2 methods.

A mixed-designed prospective study of retrospective data from orthognathic surgeries completed from November 2016 to August 2018 was performed. All models were obtained from a digital archive of the Houston Methodist oral and maxillofacial surgery department using a random table. The inclusion criteria were as follows: 1) the stone models were from patients who had undergone double-jaw orthognathic surgery; 2) the maxillary surgery had been 1-piece nonsegmental Le Fort I osteotomy; and 3) the occlusion was stable without rocking between the upper and lower dental models. Partially edentulous models were not excluded.

Data Collection

Two experienced orthodontists together mounted and articulated the 30 models manually using a Galetti articulator to their perceived ideal postoperative occlusion. To allow for standardization, the following criteria were used during the articulation: 1) coincident upper and lower dental midlines and a bilateral Class I canine relationship were the main basis of the ideal occlusion; 2) the presence of overjet and overbite and the molar relationship were weighted less; and 3) achievement of the best possible maximum contacts between the upper and lower teeth after achievement of the previous 2 clinical criteria. The orthodontist's clinical decision-making parameters were recorded in our automatic articulation algorithm later.

Once the final articulated occlusion had been determined by both orthodontists, a paper-thin bite registration was immediately fabricated using Blu-Mousse to maintain this position without creating an artificial open bite. The articulated stone models were then removed from the Galetti articulator and scanned using a CBCT scanner (iCAT, Hatfield, Pa.) using a dental model scanning protocol (0.2 mm isotropically). Each pair of models was scanned twice: first while in final occlusion with the thin-bite registration in place and tied with rubber bands and again with the upper and lower models separated and positioned randomly. Three digital models were then created: a final occlusal template model from the models scanned together and separate upper and lower models. To ensure the corresponding models were identical, the threshold for image segmentation and the parameters for the 3D reconstruction algorithm were identical for each patient using AnatomicAligner software.

The separately scanned upper dental models were digitally duplicated. To generate the control group, the final occlusal template was first registered to the lower dental model using the same registration method in the CASS planning protocol. Next, 1 of the 2 duplicated upper models was registered to the final occlusal template, resulting in manually articulated occlusion.

To generate the experimental group, the other upper dental model was automatically articulated to the lower model using the algorithm-articulated method, which had been programmed and compiled in an executable MATLAB program (MathWorks, Inc, Natick, Mass.). The recorded orthodontist's decision-making parameters were keyed into a built-in user-friendly interface, allowing the algorithm to automatically articulate the upper model to the lower model, without human intervention. During the articulation, the sole operator was kept unaware of the manually articulated occlusion in the control group. The resultant articulated models, the algorithm-articulated occlusion, served as the experimental group. Finally, the accuracy evaluation was completed qualitatively and quantitatively.

EVALUATION

The same orthodontists together evaluated the outcomes of the manually and algorithm-articulated occlusions. They were kept unaware of the method of articulation used. Both the algorithm- and manually articulated final occlusions were displayed on a large computer monitor, side by side, in random order. The evaluators were able to rotate, zoom in and out, and hide or display the models freely. They could also use the stone dental models to check the occlusion, as needed.

The same criteria used for the manual articulation were used again for the evaluation. The evaluation was completed using 3-point categorical scale (1, the occlusion on the left side of the monitor was better than that on the right side; 2, the occlusion of the 2 sides were equal; and 3, the occlusion on the left side was worse than that on the right side). Only 1 scale was assigned to each set of models.

The quantitative evaluation was performed to compare the differences in the midline, canine, and first molar regions between the 2 methods. The evaluation was completed using the local coordinate system-based method developed using the lower dental model (see FIG. 18). The measurements were performed on 5 pairs of landmarks (FIG. 22, Table 6 and FIG. 23, Table 7). The differences in the upper and lower midline, canine, and first molar relationships were calculated 3 dimensionally in the local x, y, and z axes.

Each patient had 2 upper dental models, 1 for each articulation method. To avoid human error during landmark digitization, the landmarks were only digitized using 1 randomly selected model. Next, the surface-best-fit method was used to automatically "copy" the landmarks to the other upper dental model.

After all the models had been evaluated, the results were unblinded, paired, and tabulated in an Excel spreadsheet (Microsoft Corp, Redmond, Wash.). For the qualitative evaluation results, the Wilcoxon signed-rank test was used to detect whether the differences between the 2 methods were statistically significant. For the quantitative evaluation results, repeated measures analysis of variance (ANOVA) was first used to detect whether a statistically significant difference was present between the 2 methods. The responding variable was the distance between the paired land-marks. The between-factor was the 2 methods (algorithm and manual articulations). The within-factors were the 3 dimensions (x, y, and z) and 5 locations (midline, right and left canines, and right and left first molars). The assumption for the repeated measures ANOVA was tested and could not be rejected. If a statistically significant difference was found between the 2 methods, the within contrast would be further computed and the results reported separately. If no statistically significant difference was found, the differences between the 2 methods would be presented descriptively using the mean±standard deviation.

Results

Figure 24:
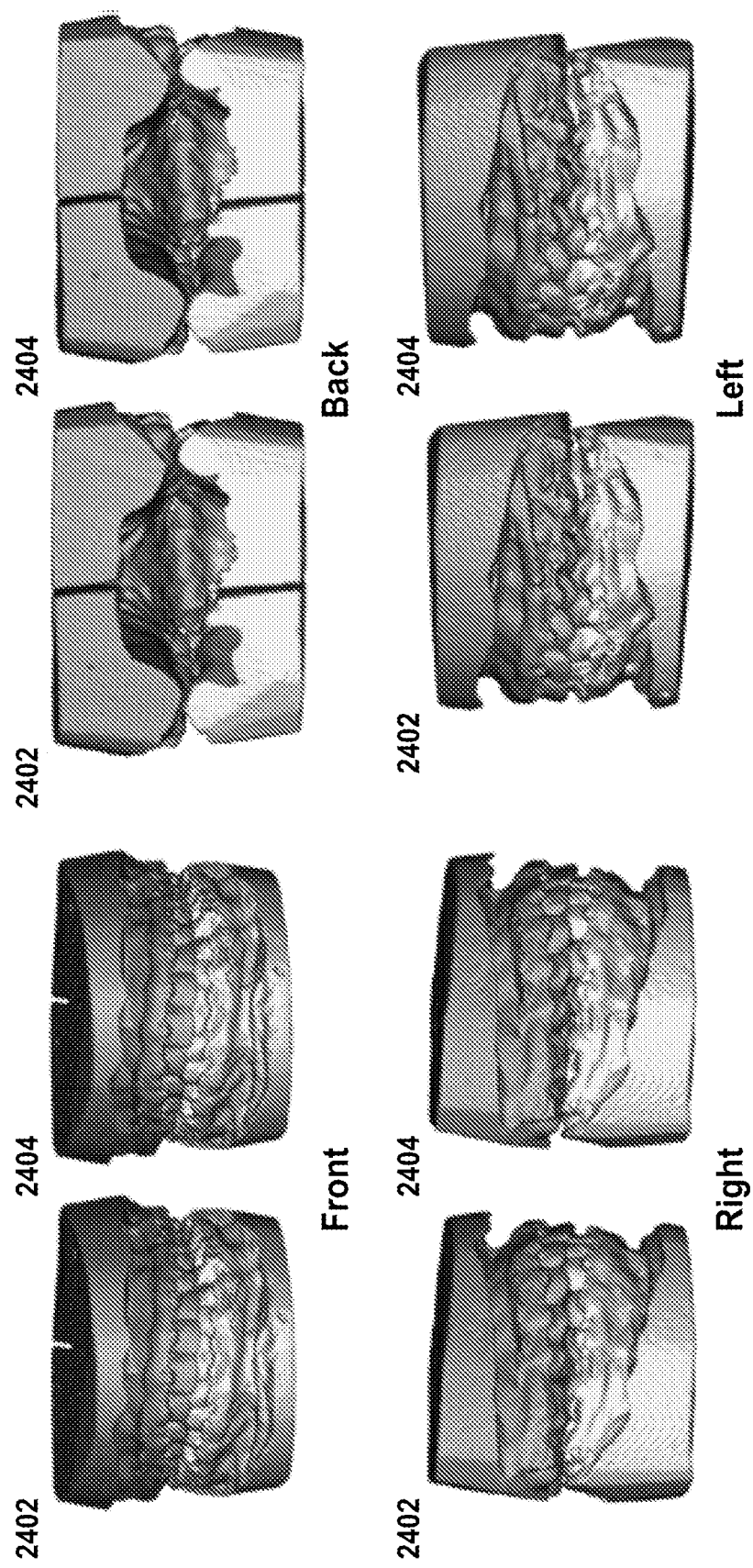
FIG. 24 illustrates a comparison of algorithm-articulated (reference number 2402) and manually-articulated (reference number 2404) occlusions from a randomly selected subject.

The qualitative evaluation results showed that the algorithm-articulated occlusion was as good as the manually articulated occlusion for all 30 pairs of models. The results of the comparison between the algorithm- and manually articulated occlusions from a randomly selected subject are shown in FIG. 24. Because no statistically significant differences were found from the qualitative evaluation, the Wilcoxon signed-rank test was not used further. The results of the repeated measures ANOVA showed no statistically significant differences in the occlusion between the 2 methods [$F(1,28)=0.03$; $P=0.87$]. Therefore, the within contrast was not computed further. The mean difference standard deviation values between the 2 methods are presented in FIG. 25, Table 8. The mean differences between the 2 methods were less than 0.2 mm in all 3 dimensions.

Discussion

The algorithm-articulated method automatically extracts the anatomy of the dental occlusal surface (the peaks and valleys) and key teeth landmarks from the digital dental models, aligns the upper and lower teeth to a clinically desired midline-canine-molar relationship, and, finally, aligns the upper and lower teeth to the best possible maximum contact without altering the midline-canine-molar relationship. The results of the present study have further confirmed that the algorithm-articulated occlusion provides results as good as those using the reference standard of the manually articulated occlusion for 1-piece Le Fort I osteotomy after orthodontists have completed the preoperative orthodontic treatment.

The algorithm-articulated method works in real-world orthodontic tooth planning. The algorithm-articulated method solves a major problem that was associated with previously developed method, in which only the MI was considered during the articulation. During preoperative orthodontics, the clinical criteria have always been prioritized to the MI. Therefore, the algorithm-articulated method was designed to use any specific clinical parameters (e.g., midline, Class I canine and molar relationships, overbite and overjet), the same as if an orthodontist determined the final occlusion using stone models. This is especially important for managing Bolton discrepancies. The algorithm will automatically resolve small Bolton discrepancies by balancing the overjet, canine, and molar relationships. However, if the Bolton discrepancies are large, users will be able to adjust the weights for the overjet, Class I canine relationship, and Class I molar relationship during the automatic articulation.

The algorithm-articulated method is also capable of articulating partially edentulous upper and lower dental arches. In experiments, 8 of the 30 patients had at least 1 or more teeth that had been extracted or were missing. The algorithm-articulated method is capable of articulating partial edentulous upper and lower arches. Dental extraction is important in achieving a Class I canine relationship. This is because the canine relationship is more important than the molar relationship for the final occlusion, and the molar relationship can be changed by the different extraction patterns of teeth. In most cases, the missing teeth were the upper and/or lower premolars. In this study, the case of 1 patient was extreme, in which 2 upper premolars were used to substitute for 2 upper canines because the canines had been used as substitutes for the lateral incisors. The same patient had also been intentionally treated to achieve a Class II molar relationship to create a Class I canine relationship using the premolar teeth and to help with surgical decompensation. In another extreme case, an upper first molar was missing. Therefore, the paired upper and lower second molars were used to achieve a Class I molar relationship on 1 side, with a standard Class I relationship for the first molars on the contralateral side, maintaining a bilateral Class I canine relationship. Two other patients had missing upper second molars; however, these were not used for calculation purposes. Nonetheless, in both extreme cases, the desired final occlusion could be established using algorithm-articulated method uneventfully.

The algorithm-articulated method is fully automatic. The data for the occlusal surface are extracted automatically, unlike the manual data extraction required for the previous method. The teeth landmarks, other than those routinely used during surgical planning, are also extracted automatically. The entire articulation process for a pair of dental models requires 3 minutes or less.

In conclusion, the results of the present evaluation have shown that digital dental models can be accurately and efficiently articulated using the standards chosen by orthodontists for 1-piece maxillary orthognathic surgery. The mean differences between the algorithm-articulated and manually articulated occlusions were within 0.2 mm. This provides a step closer to stone-less models and complete virtual planning for orthognathic surgery. Ultimately, the automatic algorithm-articulated occlusions will replace those derived from manually articulated physical dental models.

REFERENCES

[1] Xia J J, Gateno J, Teichgraeber J F, Yuan P, Chen K C, Li J, Zhang X, Tang Z, Alfi D M (2015) Algorithm for planning a double-jaw orthognathic surgery using a computer-aided surgical simulation (CASS) protocol. Part 1: planning sequence. Int J Oral Maxillofac Surg 44(12): 1431-1440.

[2] Chabanas M, Marecaux C, Payan Y, Boutault F (2002) Models for planning and simulation in computer assisted orthognathic surgery. In: Paper presented at the proceedings of the 5th international conference on medical image computing and computer-assisted intervention-Part II.

[3] Nadjmi N, Mollemans W, Daelemans A, Van Hemelen G, Schutyser F, Berge S (2010) Virtual occlusion in planning orthognathic surgical procedures. Int J Oral Maxillofac Surg 39(5):457-462.

[4] Wu W, Chen H, Cen Y, Hong Y, Khambay B, Heng P A (2017) Haptic simulation framework for determining virtual dental occlusion. Int J Comput Assist Radiol Surg 12(4):595-606.

[5] Chang Y B, Xia J J, Gateno J, Xiong Z, Zhou X, Wong S T (2010) An automatic and robust algorithm of reestablishment of digital dental occlusion. IEEE Trans Med Imaging 29(9):1652-1663.

[6] Xia J J, Chang Y B, Gateno J, Xiong Z, Zho X (2010) Auto-mated digital dental articulation. Med Image Comput Assist Interv 13(Pt 3):278-286.

[7] Deng H, Yuan P, Wong S, Gateno J, Garrett F A, Ellis R K, English J D, Jacob H B, Kim D, Xia J J (2019) An automatic approach to reestablish final dental occlusion for 1-piece maxillary orthognathic surgery. 2019 medical image computing and computer assisted intervention—MICCAI 2019. Springer, Cham, pp 345-353.

[8] Xia J J, Gateno J, Teichgraeber J F, Christensen A M, Lasky R E, Lemoine J J, Liebschner M A (2007) Accuracy of the computer-aided surgical simulation (CASS) system in the treatment of patients with complex craniomaxillofacial deformity: a pilot study. J Oral Maxillofac Surg 65(2):248-254.

[9] Hsu S S, Gateno J, Bell R B, Hirsch D L, Markiewicz M R, Teichgraeber J F, Zhou X, Xia J J (2013) Accuracy of a computer-aided surgical simulation protocol for orthognathic surgery: a prospective multicenter study. J Oral Maxillofac Surg 71(1):128-142.

[10] Bland J M, Altman D G (1986) Statistical methods for assessing agreement between two methods of clinical measurement. Lancet 1(8476):307-310

[11] Lu S, Yang J, Wang W, Li Z, Lu Z (2018) Teeth classification based on extreme learning machine. In: Paper presented at the 2018 second world conference on smart trends in systems, security and sustainability (WorldS4), 30-31 Oct. 2018.

[12] Kumar Y, Janardan R, Larson B (2012) Automatic feature identification in dental meshes. Comput Aided Des Appl 9(6):747-769.
[13] Kumar Y, Janardan R, Larson B, Moon J (2011) Improved seg-mentation of teeth in dental models. Com-put Aided Des Appl 8:211-224.
[14] Wu K, Chen L, Li J, Zhou Y (2014) Tooth segmentation on dental meshes using morphologic skeleton. Comput Gr 38:199-211.
[15] Mouritsen D A (2013) Automatic segmentation of teeth in digital dental models. University of Alabama, Birmingham.
[16] Hao W, Zhongyi L (2016) Tooth separation from dental model using segmentation field. Conf Proc IEEE Eng Med Biol Soc 2016:5616-5619.
[17] Liao S H, Liu S J, Zou B J, Ding X, Liang Y, Huang J H (2015) Automatic tooth segmentation of dental mesh based on harmonic fields. Biomed Res Int 2015:187173.
[18] Zou B J, Liu S J, Liao S H, Ding X, Liang Y (2015) Interactive tooth partition of dental mesh base on tooth-target harmonic field. Com-put Biol Med 56:132-144.
[19] Sinthanayothin C, Tharanont W (2008) Orthodontics treatment simulation by teeth segmentation and setup. In: Paper presented at the 2008 5th international conference on electrical engineer-ing/electronics, computer, telecom-munications and information technology, 14-17 May 2008.
[20] Ma Y, Li Z (2010) Computer aided orthodontics treatment by vir-tual segmentation and adjustment. In: Paper presented at the 2010 international conference on image analysis and signal processing, 9-11 Apr. 2010.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system for establishing dental occlusion, comprising:
    a processor; and
    a memory in communication with the processor, the memory having computer-executable instructions stored thereon that, when executed by the processor, cause the processor to:
    receive a maxillary dental model and a mandibular dental model;
    identify a plurality of dental landmarks in each of the maxillary and mandibular dental models, wherein the dental landmarks comprise a plurality of maxillary dental landmarks and a plurality of mandibular dental landmarks;
    extract a plurality of points-of-interest from each of the maxillary and mandibular dental models;
    align the maxillary and mandibular dental models; and
    fine tune the alignment of the maxillary and mandibular dental models to achieve maximum contact with a collision constraint, wherein the maxillary dental model comprises a plurality of individual segments, wherein the individual segments are a major segment and a minor segment, and wherein aligning the maxillary and mandibular dental models comprises:
    aligning the major segment of the maxillary dental model and the mandibular dental model by aligning a midline pair and at least one canine or embrasure pair of the maxillary and mandibular dental landmarks along a tangent line of a dental arch, and by minimizing a sum of distances between at least one molar pair of the maxillary and mandibular dental landmarks; and aligning the minor segment of the maxillary dental model and the mandibular dental model by aligning an embrasure between teeth of the major and minor segments of the maxillary dental model and at least one canine, premolar or embrasure pair of the maxillary and mandibular dental landmarks along the tangent line of the dental arch, and by minimizing a sum of distances between at least one molar pair of the maxillary and mandibular dental landmarks.

2. A computer-implemented method for establishing dental occlusion, comprising:
    receiving a maxillary dental model and a mandibular dental model;
    identifying a plurality of dental landmarks in each of the maxillary and mandibular dental models, wherein the dental landmarks comprise a plurality of maxillary dental landmarks and a plurality of mandibular dental landmarks;
    extracting a plurality of points-of-interest from each of the maxillary and mandibular dental models;
    aligning the maxillary and mandibular dental models; and
    fine tuning the alignment of the maxillary and mandibular dental models to achieve maximum contact with a collision constraint, wherein the maxillary dental model comprises a plurality of individual segments, wherein the individual segments are a major segment and a minor segment, and wherein aligning the maxillary and mandibular dental models comprises:
    aligning the major segment of the maxillary dental model and the mandibular dental model by aligning a midline pair and at least one canine or embrasure pair of the maxillary and mandibular dental landmarks along a tangent line of a dental arch, and by minimizing a sum of distances between at least one molar pair of the maxillary and mandibular dental landmarks; and
    aligning the minor segment of the maxillary dental model and the mandibular dental model by aligning an embrasure between teeth of the major and minor segments of the maxillary dental model and at least one canine, premolar or embrasure pair of the maxillary and mandibular dental landmarks along the tangent line of the dental arch, and by minimizing a sum of distances between at least one molar pair of the maxillary and mandibular dental landmarks.

3. The computer-implemented method of claim 2, further comprising adjusting the alignment of the maxillary and mandibular dental models based on user input.

4. The computer-implemented method of claim 2, wherein the points-of-interest extracted from each of the maxillary and mandibular dental models are on respective occlusal surfaces of the maxillary and mandibular dental models.

5. The computer-implemented method of claim 2, wherein extracting a plurality of points-of-interest from each of the maxillary and mandibular dental models further comprises:
    extracting respective maxillary and mandibular occlusal surface models from each of the maxillary and mandibular dental models;
    extracting the points-of-interest from the respective maxillary and mandibular occlusal surface models; and
    classifying a plurality of convex and concave points from among the points-of-interest.

6. The computer-implemented method of claim 5, further comprising:

identifying, using the convex points, a plurality of cusps on each of the respective maxillary and mandibular occlusal surface models; and identifying, using the concave points, a central groove in at least one of the respective maxillary and mandibular occlusal surface models.

7. The computer-implemented method of claim 2, wherein the dental landmarks comprise at least one of a midpoint between central incisors, a cusp point, a groove point, or an embrasure between teeth.

8. The computer-implemented method of claim 7, wherein identifying a plurality of dental landmarks in each of the maxillary and mandibular dental models further comprises receiving a location of at least one of the dental landmarks from a user.

9. The computer-implemented method of claim 7, wherein identifying a plurality of dental landmarks in each of the maxillary and mandibular dental models further comprises detecting a location of at least one of the dental landmarks.

10. The computer-implemented method of claim 2, wherein aligning the maxillary and mandibular dental models comprises aligning a midline pair and at least one canine or embrasure pair of the maxillary and mandibular dental landmarks along a tangent line of a dental arch, and minimizing a sum of distances between at least one pair of the maxillary and mandibular dental landmarks.

11. The computer-implemented method of claim 10, wherein the at least one pair of the maxillary and mandibular dental landmarks comprises at least one molar pair of the maxillary and mandibular dental landmarks.

12. The computer-implemented method of claim 2, wherein aligning the maxillary and mandibular dental models comprises aligning an upper dental curve and a lower dental curve.

13. The computer-implemented method of claim 12, further comprising extracting the upper and lower dental curves from the maxillary and mandibular dental models, respectively; estimating a respective frame of reference for each of the upper and lower dental curves; and aligning the respective frames of references of the upper and lower dental curves after registering a midline pair of the maxillary and mandibular dental landmarks.

14. The computer-implemented method of claim 2, further comprising comparing respective curves of Wilson of the aligned maxillary and mandibular dental models.

15. The computer-implemented method of claim 2, wherein the aligned maxillary and mandibular dental models represent a dental occlusion.

16. The computer-implemented method of claim 2, wherein the aligned maxillary and mandibular dental models represent an optimal position for a next stage of orthodontic treatment.

17. A computer-implemented method for establishing dental occlusion, comprising:
receiving a maxillary dental model and a mandibular dental model;
identifying a plurality of dental landmarks in each of the maxillary and mandibular dental models, wherein the dental landmarks comprise a plurality of maxillary dental landmarks and a plurality of mandibular dental landmarks;
extracting a plurality of points-of-interest from each of the maxillary and mandibular dental models;
aligning the maxillary and mandibular dental models; and
fine tuning the alignment of the maxillary and mandibular dental models to achieve maximum contact with a collision constraint, wherein the maxillary dental model comprises a plurality of individual segments, wherein the individual segments are a right segment and a left segment, and wherein aligning the maxillary and mandibular dental models comprises:
aligning a right segment of the maxillary dental model and the mandibular dental model by aligning a midline pair and at least one canine or embrasure pair of the maxillary and mandibular dental landmarks along a tangent line of a dental arch, and by minimizing a sum of distances at least one molar pair of the maxillary and mandibular dental landmarks; and
aligning a left segment of the maxillary dental model and the mandibular dental model by aligning a midline pair and at least one canine or embrasure pair of maxillary and mandibular dental landmarks along the tangent line of the dental arch, and by minimizing a sum of distances between at least one molar pair of the maxillary and mandibular dental landmarks.

18. The computer-implemented method of claim 17, further comprising comparing respective curves of Wilson of the aligned maxillary and mandibular dental models.

19. A computer-implemented method for establishing dental occlusion, comprising:
receiving a maxillary dental model and a mandibular dental model, wherein the maxillary dental model comprises a plurality of individual segments, the individual segments comprising an anterior segment and left and right posterior segments;
identifying a plurality of dental landmarks in each of the maxillary and mandibular dental models, wherein the dental landmarks comprise a plurality of maxillary dental landmarks and a plurality of mandibular dental landmarks;
extracting a plurality of points-of-interest from each of the maxillary and mandibular dental models;
aligning the maxillary and mandibular dental models;
fine tuning the alignment of the maxillary and mandibular dental models to achieve maximum contact with a collision constraint;
receiving an overbite; and
receiving an overjet, wherein aligning the maxillary and mandibular dental models comprises:
aligning the maxillary and mandibular dental models by aligning a midline pair of the maxillary and mandibular dental landmarks along a tangent line of a dental arch, by considering a curvature of the anterior segment of the maxillary dental model to a curvature of the mandibular dental model, and by minimizing a sum of distances between at least one pair of the points-of-interests of the maxillary and mandibular incisors; and
aligning each of the left and right posterior segments of the maxillary dental model and the mandibular dental model by aligning an embrasure between teeth of the anterior and posterior segments of the maxillary dental model and at least one canine, premolar, or embrasure pair of the maxillary and mandibular dental landmarks along the tangent line of the dental arch, and by minimizing a sum of distances between at least one molar pair of the maxillary and mandibular dental landmarks.

20. The computer-implemented method of claim 19, further comprising iteratively aligning the maxillary and mandibular dental models for each of a plurality of overbites and/or overjets.

21. The computer-implemented method of claim 20, further comprising ranking the iteratively aligned maxillary and mandibular dental models.

22. The computer-implemented method of claim 19, further comprising comparing respective curves of Wilson of the aligned maxillary and mandibular dental models.

* * * * *